United States Patent
Fox et al.

(10) Patent No.: US 11,464,659 B2
(45) Date of Patent: *Oct. 11, 2022

(54) CRIMPING DEVICE FOR LOADING STENTS AND PROSTHETIC HEART VALVES

(71) Applicant: Twelve, Inc., Redwood City, CA (US)

(72) Inventors: Jason Fox, San Mateo, CA (US); David Trask, Redwood City, CA (US)

(73) Assignee: Twelve, Inc., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/927,238

(22) Filed: Jul. 13, 2020

(65) Prior Publication Data
US 2020/0337872 A1     Oct. 29, 2020

Related U.S. Application Data

(63) Continuation of application No. 15/615,144, filed on Jun. 6, 2017, now Pat. No. 10,709,591.

(51) Int. Cl.
*A61F 2/95*         (2013.01)
*B23P 19/02*        (2006.01)
(Continued)

(52) U.S. Cl.
CPC .............. *A61F 2/95* (2013.01); *A61F 2/2427* (2013.01); *A61F 2/9524* (2020.05);
(Continued)

(58) Field of Classification Search
CPC ........ A61F 2/2427; A61F 2/95; A61F 2/9525; A61F 2/958; A61F 2002/9522;
(Continued)

(56) References Cited

U.S. PATENT DOCUMENTS 3,526,219 A    9/1970   Balamuth
3,565,062 A    2/1971   Kuris
(Continued)

FOREIGN PATENT DOCUMENTS

CN    1440261 A      9/2003
CN    101076290 A    11/2007
(Continued)

OTHER PUBLICATIONS

US 9,265,606 B2, 02/2016, Buchbinder et al. (withdrawn)
(Continued)

*Primary Examiner* — Jermie E Cozart
(74) *Attorney, Agent, or Firm* — Medler Ferro Woodhouse & Mills PLLC

(57) ABSTRACT

Systems and devices for crimping a medical device and associated methods are disclosed herein. A crimping device configured in accordance with embodiments of the present technology can include, for example, a frame including a stationary plate, a movable member, and a plurality of blades arranged to form a channel and each including a pin that projects through a slot on the movable member and a corresponding slot on the stationary plate. The crimping device can be actuated to move the movable member relative to the stationary plate to drive the pins along paths defined by the slots to thereby drive the blades radially inward to crimp a medical device positioned within the channel.

19 Claims, 7 Drawing Sheets

(51) Int. Cl.
*A61F 2/24* (2006.01)
*B21D 39/04* (2006.01)
*A61F 2/958* (2013.01)
*B23P 11/02* (2006.01)
*H01R 43/048* (2006.01)
*H01R 43/04* (2006.01)

(52) U.S. Cl.
CPC ............ *A61F 2/9525* (2020.05); *B23P 19/02* (2013.01); *A61F 2/958* (2013.01); *A61F 2/9522* (2020.05); *A61F 2002/9583* (2013.01); *A61F 2240/001* (2013.01); *B21D 39/046* (2013.01); *B23P 11/025* (2013.01); *H01R 43/04* (2013.01); *H01R 43/048* (2013.01)

(58) Field of Classification Search
CPC ........ A61F 2002/9583; A61F 2240/001; A61F 2/9522; B23P 11/025; B23P 19/02; B21D 39/046; H01R 43/04; H01R 43/048
See application file for complete search history.

(56) References Cited

U.S. PATENT DOCUMENTS

| | | |
|---|---|---|
| 3,589,363 A | 6/1971 | Banko et al. |
| 3,667,474 A | 6/1972 | Lapkin et al. |
| 3,823,717 A | 7/1974 | Pohlman et al. |
| 3,861,391 A | 1/1975 | Antonevich et al. |
| 3,896,811 A | 7/1975 | Storz |
| 4,042,979 A | 8/1977 | Angell |
| 4,188,952 A | 2/1980 | Loschilov et al. |
| 4,388,735 A | 6/1983 | Ionescu et al. |
| 4,423,525 A | 1/1984 | Vallana et al. |
| 4,431,006 A | 2/1984 | Trimmer et al. |
| 4,441,216 A | 4/1984 | Ionescu et al. |
| 4,445,509 A | 5/1984 | Auth |
| 4,484,579 A | 11/1984 | Meno et al. |
| 4,490,859 A | 1/1985 | Black et al. |
| 4,587,958 A | 5/1986 | Noguchi et al. |
| 4,589,419 A | 5/1986 | Lauqhlin et al. |
| 4,602,911 A | 7/1986 | Ahmadi et al. |
| 4,629,459 A | 12/1986 | Ionescu et al. |
| 4,646,736 A | 3/1987 | Auth |
| 4,653,577 A | 3/1987 | Noda |
| 4,666,442 A | 5/1987 | Arru et al. |
| 4,679,556 A | 7/1987 | Lubock et al. |
| 4,692,139 A | 9/1987 | Stiles |
| 4,747,821 A | 5/1988 | Kensey et al. |
| 4,750,902 A | 6/1988 | Wuchinich et al. |
| 4,758,151 A | 7/1988 | Arru et al. |
| 4,777,951 A | 10/1988 | Cribier et al. |
| 4,787,388 A | 11/1988 | Hofmann |
| 4,796,629 A | 1/1989 | Grayzel |
| 4,808,153 A | 2/1989 | Parisi |
| 4,819,751 A | 4/1989 | Shimada et al. |
| 4,841,977 A | 6/1989 | Griffith et al. |
| 4,870,953 A | 10/1989 | DonMicheal et al. |
| 4,878,495 A | 11/1989 | Grayzel |
| 4,892,540 A | 1/1990 | Vallana |
| 4,898,575 A | 2/1990 | Fischell et al. |
| 4,909,252 A | 3/1990 | Goldberger |
| 4,919,133 A | 4/1990 | Chiang |
| 4,920,954 A | 5/1990 | Alliger et al. |
| 4,936,281 A | 6/1990 | Stasz |
| 4,960,411 A | 10/1990 | Buchbinder |
| 4,986,830 A | 1/1991 | Owens et al. |
| 4,990,134 A | 2/1991 | Auth |
| 5,002,567 A | 3/1991 | Bona et al. |
| 5,058,570 A | 10/1991 | Idemoto et al. |
| 5,069,664 A | 12/1991 | Guess et al. |
| 5,076,276 A | 12/1991 | Sakurai et al. |
| 5,084,151 A | 1/1992 | Vallana et al. |
| 5,104,406 A | 4/1992 | Curcio et al. |
| 5,106,302 A | 4/1992 | Farzin-Nia et al. |
| 5,248,296 A | 9/1993 | Alliger |
| 5,267,954 A | 12/1993 | Nita |
| 5,269,291 A | 12/1993 | Carter |
| 5,295,958 A | 3/1994 | Shturman |
| 5,304,115 A | 4/1994 | Pflueger et al. |
| 5,314,407 A | 5/1994 | Auth et al. |
| 5,318,014 A | 6/1994 | Carter |
| 5,332,402 A | 7/1994 | Teitelbaum |
| 5,344,426 A | 9/1994 | Lau et al. |
| 5,352,199 A | 10/1994 | Tower |
| 5,356,418 A | 10/1994 | Shturman |
| 5,370,684 A | 12/1994 | Vallana et al. |
| 5,387,247 A | 2/1995 | Vallana et al. |
| 5,397,293 A | 3/1995 | Alliger et al. |
| 5,411,552 A | 5/1995 | Andersen et al. |
| 5,443,446 A | 8/1995 | Shturman |
| 5,449,373 A | 9/1995 | Pinchasik et al. |
| 5,489,297 A | 2/1996 | Duran |
| 5,584,879 A | 12/1996 | Reimold et al. |
| 5,609,151 A | 3/1997 | Mulier et al. |
| 5,626,603 A | 5/1997 | Venturelli et al. |
| 5,656,036 A | 8/1997 | Palmaz |
| 5,662,671 A | 9/1997 | Barbut et al. |
| 5,681,336 A | 10/1997 | Clement et al. |
| 5,695,507 A | 12/1997 | Auth et al. |
| 5,713,953 A | 2/1998 | Vallana et al. |
| 5,725,494 A | 3/1998 | Brisken |
| 5,782,931 A | 7/1998 | Yang et al. |
| 5,817,101 A | 10/1998 | Fiedler |
| 5,827,229 A | 10/1998 | Auth et al. |
| 5,827,321 A | 10/1998 | Roubin et al. |
| 5,840,081 A | 11/1998 | Andersen et al. |
| 5,853,422 A | 12/1998 | Huebsch et al. |
| 5,855,601 A | 1/1999 | Bessler et al. |
| 5,868,781 A | 2/1999 | Killion |
| 5,873,811 A | 2/1999 | Wang et al. |
| 5,873,812 A | 2/1999 | Ciana et al. |
| 5,904,679 A | 5/1999 | Clayman |
| 5,957,882 A | 9/1999 | Nita et al. |
| 5,972,004 A | 10/1999 | Williamson, IV et al. |
| 5,989,208 A | 11/1999 | Nita |
| 5,989,280 A | 11/1999 | Euteneuer et al. |
| 6,047,700 A | 4/2000 | Eggers et al. |
| 6,056,759 A | 5/2000 | Fiedler |
| 6,085,754 A | 7/2000 | Alferness et al. |
| 6,113,608 A | 9/2000 | Monroe et al. |
| RE36,939 E | 10/2000 | Tachibana et al. |
| 6,129,734 A | 10/2000 | Shturman et al. |
| 6,132,444 A | 10/2000 | Shturman et al. |
| 6,168,579 B1 | 1/2001 | Tsuaita |
| 6,217,595 B1 | 4/2001 | Shturman et al. |
| 6,254,635 B1 | 7/2001 | Schroeder et al. |
| 6,295,712 B1 | 10/2001 | Shturman et al. |
| 6,306,414 B1 | 10/2001 | Koike |
| 6,321,109 B2 | 11/2001 | Ben-Haim et al. |
| 6,402,679 B1 | 6/2002 | Mortier et al. |
| 6,423,032 B2 | 7/2002 | Parodi |
| 6,425,916 B1 | 7/2002 | Garrison et al. |
| 6,440,164 B1 | 8/2002 | DiMatteo et al. |
| 6,454,737 B1 | 9/2002 | Nita et al. |
| 6,454,757 B1 | 9/2002 | Nita et al. |
| 6,454,799 B1 | 9/2002 | Schreck |
| 6,458,153 B1 | 10/2002 | Bailey et al. |
| 6,461,382 B1 | 10/2002 | Cao |
| 6,494,890 B1 | 12/2002 | Shturman et al. |
| 6,494,891 B1 | 12/2002 | Cornish et al. |
| 6,505,080 B1 | 1/2003 | Sutton |
| 6,530,952 B2 | 3/2003 | Vesely |
| 6,540,782 B1 | 4/2003 | Snvders |
| 6,562,067 B2 | 5/2003 | Mathis |
| 6,565,588 B1 | 5/2003 | Clement et al. |
| 6,569,196 B1 | 5/2003 | Vesely |
| 6,579,308 B1 | 6/2003 | Jansen et al. |
| 6,582,462 B1 | 6/2003 | Andersen et al. |
| 6,595,912 B2 | 7/2003 | Lau et al. |
| 6,605,109 B2 | 8/2003 | Fiedler |
| 6,616,689 B1 | 9/2003 | Ainsworth et al. |
| 6,623,452 B2 | 9/2003 | Chien et al. |
| 6,638,288 B1 | 10/2003 | Shturman et al. |
| 6,648,854 B1 | 11/2003 | Patterson et al. |

(56) References Cited

U.S. PATENT DOCUMENTS

| | | |
|---|---|---|
| 6,689,086 B1 | 2/2004 | Nita et al. |
| 6,702,748 B1 | 3/2004 | Nita et al. |
| 6,730,121 B2 | 5/2004 | Ortiz et al. |
| 6,746,463 B1 | 6/2004 | Schwartz |
| 6,811,801 B2 | 11/2004 | Nguyen et al. |
| 6,818,001 B2 | 11/2004 | Wulfman et al. |
| 6,843,797 B2 | 1/2005 | Nash et al. |
| 6,852,118 B2 | 2/2005 | Shturman et al. |
| 6,855,123 B2 | 2/2005 | Nita |
| 6,869,439 B2 | 3/2005 | White et al. |
| 6,951,571 B1 | 10/2005 | Srivastava |
| 6,986,775 B2 | 1/2006 | Morales et al. |
| 7,018,404 B2 | 3/2006 | Holmberg et al. |
| 7,052,487 B2 | 5/2006 | Cohn et al. |
| 7,077,861 B2 | 7/2006 | Spence |
| 7,125,420 B2 | 10/2006 | Rourke et al. |
| 7,186,264 B2 | 3/2007 | Liddicoat et al. |
| 7,220,277 B2 | 5/2007 | Arru et al. |
| 7,261,732 B2 | 8/2007 | Justino |
| 7,296,577 B2 | 11/2007 | Lashinski et al. |
| 7,381,218 B2 | 6/2008 | Schreck |
| 7,404,824 B1 | 7/2008 | Webler et al. |
| 7,442,204 B2 | 10/2008 | Schwammenthal et al. |
| 7,473,275 B2 | 1/2009 | Marquez |
| 7,510,575 B2 | 3/2009 | Spenser et al. |
| 7,585,321 B2 | 9/2009 | Cribier |
| 7,588,582 B2 | 9/2009 | Starksen et al. |
| 7,621,948 B2 | 11/2009 | Herrmann et al. |
| 7,636,997 B2 | 12/2009 | Perreault et al. |
| 7,708,775 B2 | 5/2010 | Rowe et al. |
| 7,748,389 B2 | 7/2010 | Salahieh et al. |
| 7,753,922 B2 | 7/2010 | Starksen |
| 7,753,949 B2 | 7/2010 | Lamphere et al. |
| 7,803,168 B2 | 9/2010 | Gifford et al. |
| 7,857,845 B2 | 12/2010 | Stacchino et al. |
| 7,896,915 B2 | 3/2011 | Guyenot et al. |
| 7,942,928 B2 | 5/2011 | Webler et al. |
| 7,992,273 B2 | 8/2011 | Austin |
| 7,993,392 B2 | 8/2011 | Righini et al. |
| 8,002,826 B2 | 8/2011 | Seguin |
| 8,006,535 B2 | 8/2011 | Righini et al. |
| 8,034,103 B2 | 10/2011 | Burriesci et al. |
| 8,052,750 B2 | 11/2011 | Tuval et al. |
| 8,057,539 B2 | 11/2011 | Ghione et al. |
| 8,062,355 B2 | 11/2011 | Figulla et al. |
| 8,070,799 B2 | 12/2011 | Righini et al. |
| 8,109,996 B2 | 2/2012 | Stacchino et al. |
| 8,114,154 B2 | 2/2012 | Righini et al. |
| 8,252,051 B2 | 8/2012 | Chau et al. |
| 8,353,953 B2 | 1/2013 | Giannetti et al. |
| 8,398,704 B2 | 3/2013 | Straubinger et al. |
| 8,403,981 B2 | 3/2013 | Forster et al. |
| 8,403,982 B2 | 3/2013 | Giannetti et al. |
| 8,403,983 B2 | 3/2013 | Quadri et al. |
| 8,414,643 B2 | 4/2013 | Tuval et al. |
| 8,449,599 B2 | 5/2013 | Chau et al. |
| 8,470,024 B2 | 6/2013 | Ghione et al. |
| 8,486,137 B2 | 6/2013 | Suri et al. |
| 8,475,521 B2 | 7/2013 | Suri et al. |
| 8,496,671 B1 | 7/2013 | Hausen |
| 8,512,252 B2 | 8/2013 | Ludomirsky et al. |
| 8,512,397 B2 | 8/2013 | Rolando et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,539,662 B2 | 9/2013 | Stacchino et al. |
| 8,540,767 B2 | 9/2013 | Zhanq |
| 8,540,768 B2 | 9/2013 | Stacchino et al. |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 | 12/2013 | Gross et al. |
| 8,623,077 B2 | 1/2014 | Cohn |
| 8,628,566 B2 | 1/2014 | Eberhardt et al. |
| 8,632,585 B2 | 1/2014 | Seguin et al. |
| 8,632,586 B2 | 1/2014 | Spenser et al. |
| 8,634,935 B2 | 1/2014 | Gaudiani |
| 8,640,521 B2 | 2/2014 | Righini et al. |
| 8,647,254 B2 | 2/2014 | Callas et al. |
| 8,652,203 B2 | 2/2014 | Quadri et al. |
| 8,652,204 B2 | 2/2014 | Quill et al. |
| 8,657,872 B2 | 2/2014 | Seguin |
| 8,672,998 B2 | 3/2014 | Lichtenstein et al. |
| 8,673,001 B2 | 3/2014 | Cartledge et al. |
| 8,679,176 B2 | 3/2014 | Matheny |
| 8,685,086 B2 | 4/2014 | Navia et al. |
| 8,688,234 B2 | 4/2014 | Zhu et al. |
| 8,690,858 B2 | 4/2014 | Machold et al. |
| 8,709,074 B2 | 4/2014 | Solem et al. |
| 8,712,133 B2 | 4/2014 | Guhring et al. |
| 8,715,160 B2 | 5/2014 | Raman et al. |
| 8,715,207 B2 | 5/2014 | Righini et al. |
| 8,721,665 B2 | 5/2014 | Oz et al. |
| 8,721,718 B2 | 5/2014 | Kassab |
| 8,740,918 B2 | 6/2014 | Seguin |
| 8,747,460 B2 | 6/2014 | Tuval et al. |
| 8,758,431 B2 | 6/2014 | Orlov et al. |
| 8,758,432 B2 | 6/2014 | Solem |
| 8,771,292 B2 | 7/2014 | Allen et al. |
| 8,771,345 B2 | 7/2014 | Tuval et al. |
| 8,771,346 B2 | 7/2014 | Tuval et al. |
| 8,777,991 B2 | 7/2014 | Zarbatany et al. |
| 8,778,016 B2 | 7/2014 | Janovsky et al. |
| 8,781,580 B2 | 7/2014 | Hedberg et al. |
| 8,784,482 B2 | 7/2014 | Rahdert et al. |
| 8,792,699 B2 | 7/2014 | Guetter et al. |
| 8,795,356 B2 | 8/2014 | Quadri et al. |
| 8,801,779 B2 | 8/2014 | Sequin et al. |
| 8,808,356 B2 | 8/2014 | Braido et al. |
| 8,808,366 B2 | 8/2014 | Braido et al. |
| 8,808,367 B2 | 8/2014 | Suri et al. |
| 8,812,431 B2 | 8/2014 | Voigt et al. |
| 8,828,043 B2 | 9/2014 | Chambers |
| 8,834,563 B2 | 9/2014 | Righini |
| 8,840,661 B2 | 9/2014 | Manasse |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 8,858,622 B2 | 10/2014 | Machold et al. |
| 8,859,724 B2 | 10/2014 | Meier et al. |
| 8,864,822 B2 | 10/2014 | Spence et al. |
| 8,870,936 B2 | 10/2014 | Rowe |
| 8,870,948 B1 | 10/2014 | Erzberger et al. |
| 8,870,949 B2 | 10/2014 | Rowe |
| 8,894,702 B2 | 11/2014 | Quadri et al. |
| 8,900,295 B2 | 12/2014 | Migliazza et al. |
| 8,920,492 B2 | 12/2014 | Stacchino et al. |
| 8,926,694 B2 | 1/2015 | Costello |
| 8,932,348 B2 | 1/2015 | Solem et al. |
| 8,951,285 B2 | 2/2015 | Suaimoto et al. |
| 8,961,597 B2 | 2/2015 | Subramanian et al. |
| 8,968,393 B2 | 3/2015 | Rothstein |
| 8,968,395 B2 | 3/2015 | Hauser et al. |
| 8,974,445 B2 | 3/2015 | Warnking et al. |
| 8,979,922 B2 | 3/2015 | Jayasinghe et al. |
| 8,979,923 B2 | 3/2015 | Spence et al. |
| 8,986,370 B2 | 3/2015 | Annest |
| 8,986,376 B2 | 3/2015 | Solem |
| 8,992,604 B2 | 3/2015 | Gross et al. |
| 9,011,522 B2 | 4/2015 | Annest |
| 9,011,523 B2 | 4/2015 | Seguin |
| 9,017,399 B2 | 4/2015 | Gross et al. |
| 9,023,098 B2 | 5/2015 | Kuehn |
| 9,023,100 B2 | 5/2015 | Quadri et al. |
| 9,050,188 B2 | 6/2015 | Schweich, Jr. et al. |
| 9,056,008 B2 | 6/2015 | Righini et al. |
| 9,066,800 B2 | 6/2015 | Clague et al. |
| 9,084,676 B2 | 7/2015 | Chau et al. |

(56) References Cited

U.S. PATENT DOCUMENTS

| | | |
|---|---|---|
| 9,095,433 B2 | 8/2015 | Lutter et al. |
| 9,114,010 B2 | 8/2015 | Gaschino et al. |
| 9,119,713 B2 | 9/2015 | Board et al. |
| 9,132,009 B2 | 9/2015 | Hacohen et al. |
| 9,138,312 B2 | 9/2015 | Tuval et al. |
| 9,138,313 B2 | 9/2015 | McGuckin, Jr. et al. |
| 9,138,314 B2 | 9/2015 | Rolando et al. |
| 9,149,207 B2 | 10/2015 | Sauter et al. |
| 9,161,836 B2 | 10/2015 | Rolando et al. |
| 9,168,105 B2 | 10/2015 | Giannetti et al. |
| 9,180,005 B1 | 11/2015 | Lashinski et al. |
| 9,186,249 B2 | 11/2015 | Rolando et al. |
| 9,192,466 B2 | 11/2015 | Kovalsky et al. |
| 9,192,471 B2 | 11/2015 | Bolling |
| 9,204,819 B2 | 12/2015 | Grunwald et al. |
| 9,232,942 B2 | 1/2016 | Seguin et al. |
| 9,232,999 B2 | 1/2016 | Maurer et al. |
| 9,241,790 B2 | 1/2016 | Lane et al. |
| 9,248,014 B2 | 2/2016 | Lane et al. |
| 9,248,017 B2 | 2/2016 | Rolando et al. |
| 9,254,192 B2 | 2/2016 | Lutter et al. |
| 9,271,833 B2 | 3/2016 | Kim et al. |
| 9,289,289 B2 | 3/2016 | Rolando et al. |
| 9,289,291 B2 | 3/2016 | Gorman, III et al. |
| 9,289,297 B2 | 3/2016 | Wilson et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,339,207 B2 | 5/2016 | Grunwald et al. |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,358,105 B2 | 6/2016 | Marchisio et al. |
| 9,358,108 B2 | 6/2016 | Bortlein et al. |
| 9,387,075 B2 | 7/2016 | Bortlein et al. |
| 9,387,078 B2 | 7/2016 | Gross et al. |
| 9,393,111 B2 | 7/2016 | Ma et al. |
| 9,421,094 B2 | 8/2016 | Schweich, Jr. et al. |
| 9,433,574 B2 | 9/2016 | Martin et al. |
| 9,480,559 B2 | 11/2016 | Vidlund et al. |
| 9,486,313 B2 | 11/2016 | Stacchino et al. |
| 9,504,835 B2 | 11/2016 | Graindorge |
| 9,629,719 B2 | 4/2017 | Rothstein et al. |
| 9,675,454 B2 | 6/2017 | Vidlund et al. |
| 9,681,951 B2 | 6/2017 | Ratz et al. |
| 9,687,342 B2 | 6/2017 | Figulla et al. |
| 9,687,343 B2 | 6/2017 | Bortlein et al. |
| 9,693,859 B2 | 7/2017 | Braido et al. |
| 9,693,862 B2 | 7/2017 | Campbell et al. |
| 9,694,121 B2 | 7/2017 | Alexander et al. |
| 9,700,409 B2 | 7/2017 | Braido et al. |
| 9,700,411 B2 | 7/2017 | Klima et al. |
| 9,700,413 B2 | 7/2017 | Ruyra Baliarda et al. |
| 9,730,791 B2 | 8/2017 | Ratz et al. |
| 9,730,794 B2 | 8/2017 | Carpentier et al. |
| 9,750,605 B2 | 9/2017 | Ganesan et al. |
| 9,750,606 B2 | 9/2017 | Ganesan et al. |
| 9,750,607 B2 | 9/2017 | Ganesan et al. |
| 9,763,657 B2 | 9/2017 | Hacohen et al. |
| 9,763,658 B2 | 9/2017 | Eigler et al. |
| 9,763,782 B2 | 9/2017 | Solem et al. |
| 9,770,328 B2 | 9/2017 | Macoviak et al. |
| 9,788,931 B2 | 10/2017 | Giordano et al. |
| 9,801,717 B2 | 10/2017 | Edquist et al. |
| 9,827,092 B2 | 11/2017 | Vidlund et al. |
| 9,827,101 B2 | 11/2017 | Solem et al. |
| 9,833,313 B2 | 12/2017 | Board et al. |
| 9,833,315 B2 | 12/2017 | Vidlund et al. |
| 9,839,511 B2 | 12/2017 | Ma et al. |
| 9,844,435 B2 | 12/2017 | Eidenschink |
| 9,848,880 B2 | 12/2017 | Coleman et al. |
| 9,848,981 B2 | 12/2017 | Suri et al. |
| 9,848,983 B2 | 12/2017 | Lashinski et al. |
| 9,861,477 B2 | 1/2018 | Backus et al. |
| 9,861,480 B2 | 1/2018 | Zakai et al. |
| 9,867,695 B2 | 1/2018 | Stacchino et al. |
| 9,895,223 B2 | 2/2018 | Stacchino et al. |
| 9,895,225 B2 | 2/2018 | Rolando et al. |
| 9,918,841 B2 | 3/2018 | Righini et al. |
| 9,974,647 B2 | 5/2018 | Ganesan et al. |
| 10,058,313 B2 | 8/2018 | Manasse |
| 10,065,032 B2 | 9/2018 | Ollivier |
| 10,098,733 B2 | 10/2018 | Righini |
| 10,117,741 B2 | 11/2018 | Schweich, Jr. et al. |
| 10,143,550 B2 | 12/2018 | Achiluzzi |
| 10,213,301 B2 | 2/2019 | Ganesan et al. |
| 10,245,141 B2 | 4/2019 | Ghione et al. |
| 10,265,166 B2 | 4/2019 | Schweich, Jr. et al. |
| 10,285,810 B2 | 5/2019 | Schweich, Jr. et al. |
| 10,449,039 B2 | 10/2019 | Ganesan et al. |
| 10,709,591 B2 * | 7/2020 | Fox ................ B23P 19/02 |
| 2001/0021872 A1 | 9/2001 | Bailey et al. |
| 2001/0049492 A1 | 12/2001 | Frazier et al. |
| 2002/0007219 A1 | 1/2002 | Merrill et al. |
| 2002/0013571 A1 | 1/2002 | Goldfarb et al. |
| 2002/0072792 A1 | 6/2002 | Burgermeister et al. |
| 2002/0082637 A1 | 6/2002 | Lumauia |
| 2002/0099439 A1 | 7/2002 | Schwartz et al. |
| 2002/0138138 A1 | 9/2002 | Yang |
| 2002/0151970 A1 | 10/2002 | Garrison et al. |
| 2002/0173841 A1 | 11/2002 | Ortiz et al. |
| 2002/0188350 A1 | 12/2002 | Arru et al. |
| 2003/0120340 A1 | 6/2003 | Liska et al. |
| 2003/0139689 A1 | 7/2003 | Shturman et al. |
| 2004/0006358 A1 | 1/2004 | Wulfman et al. |
| 2004/0039412 A1 | 2/2004 | Isshiki et al. |
| 2004/0044350 A1 | 3/2004 | Martin et al. |
| 2004/0057955 A1 | 3/2004 | O'Brien et al. |
| 2004/0082910 A1 | 4/2004 | Constantz et al. |
| 2004/0092858 A1 | 5/2004 | Wilson et al. |
| 2004/0092962 A1 | 5/2004 | Thornton et al. |
| 2004/0092989 A1 | 5/2004 | Wilson et al. |
| 2004/0106989 A1 | 6/2004 | Wilson et al. |
| 2004/0117009 A1 | 6/2004 | Cali et al. |
| 2004/0122510 A1 | 6/2004 | Sarac |
| 2004/0127979 A1 | 7/2004 | Wilson et al. |
| 2004/0127982 A1 | 7/2004 | Machold et al. |
| 2004/0186558 A1 | 9/2004 | Pavcnik et al. |
| 2004/0199191 A1 | 10/2004 | Schwartz |
| 2004/0230117 A1 | 11/2004 | Tosaya et al. |
| 2004/0230212 A1 | 11/2004 | Wulfman |
| 2004/0230213 A1 | 11/2004 | Wulfman et al. |
| 2004/0243162 A1 | 12/2004 | Wulfman et al. |
| 2005/0007219 A1 | 1/2005 | Ma et al. |
| 2005/0075662 A1 | 4/2005 | Pedersen et al. |
| 2005/0075720 A1 | 4/2005 | Nguyen et al. |
| 2005/0075727 A1 | 4/2005 | Wheatley |
| 2005/0107661 A1 | 5/2005 | Lau et al. |
| 2005/0137682 A1 | 6/2005 | Justino |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137700 A1 | 6/2005 | Spence et al. |
| 2005/0137701 A1 | 6/2005 | Salahieh et al. |
| 2005/0137702 A1 | 6/2005 | Haug et al. |
| 2005/0183259 A1 | 8/2005 | Eidenschink et al. |
| 2005/0188525 A1 | 9/2005 | Weber et al. |
| 2005/0228477 A1 | 10/2005 | Grainger et al. |
| 2005/0267523 A1 | 12/2005 | Devellian et al. |
| 2005/0273135 A1 | 12/2005 | Chanduszko |
| 2006/0058872 A1 | 3/2006 | Salahieh et al. |
| 2006/0106456 A9 | 5/2006 | Machold et al. |
| 2006/0149360 A1 | 7/2006 | Schwammenthal et al. |
| 2006/0167543 A1 | 7/2006 | Bailey et al. |
| 2006/0195183 A1 | 8/2006 | Navia et al. |
| 2006/0253191 A1 | 11/2006 | Salahieh et al. |
| 2006/0287719 A1 | 12/2006 | Rowe et al. |
| 2007/0056346 A1 | 3/2007 | Spencer et al. |
| 2007/0061010 A1 | 3/2007 | Hauser et al. |
| 2007/0073391 A1 | 3/2007 | Bourang et al. |

(56) References Cited

U.S. PATENT DOCUMENTS

| | | |
|---|---|---|
| 2007/0078302 A1 | 4/2007 | Ortiz et al. |
| 2007/0088431 A1 | 4/2007 | Bourana et al. |
| 2007/0142906 A1 | 6/2007 | Figulla et al. |
| 2007/0173932 A1 | 7/2007 | Cali et al. |
| 2008/0071369 A1 | 3/2008 | Tuval et al. |
| 2008/0082166 A1 | 4/2008 | Styrc et al. |
| 2008/0103586 A1 | 5/2008 | Styrc et al. |
| 2008/0140189 A1 | 6/2008 | Nguyen et al. |
| 2008/0147181 A1 | 6/2008 | Ghione et al. |
| 2008/0208332 A1 | 8/2008 | Lamphere et al. |
| 2008/0221672 A1 | 9/2008 | Lamphere et al. |
| 2008/0234728 A1 | 9/2008 | Starksen et al. |
| 2008/0243245 A1 | 10/2008 | Thambar et al. |
| 2008/0243246 A1 | 10/2008 | Ryan et al. |
| 2008/0262603 A1 | 10/2008 | Giaquinta et al. |
| 2009/0054969 A1 | 2/2009 | Salahieh et al. |
| 2009/0076586 A1 | 3/2009 | Hauser et al. |
| 2009/0076598 A1 | 3/2009 | Salahieh et al. |
| 2009/0093670 A1 | 4/2009 | Annest et al. |
| 2009/0105794 A1 | 4/2009 | Ziarno et al. |
| 2009/0157174 A1 | 6/2009 | Yoganathan et al. |
| 2009/0164006 A1 | 6/2009 | Seguin et al. |
| 2009/0198315 A1 | 8/2009 | Boudjemline |
| 2009/0216312 A1 | 8/2009 | Straubinaer et al. |
| 2009/0240320 A1 | 9/2009 | Tuval et al. |
| 2009/0259292 A1 | 10/2009 | Bonhoeffer |
| 2009/0259306 A1 | 10/2009 | Rowe |
| 2009/0264997 A1 | 10/2009 | Salahieh et al. |
| 2009/0276040 A1 | 11/2009 | Rowe et al. |
| 2009/0281609 A1 | 11/2009 | Benichou et al. |
| 2009/0281618 A1 | 11/2009 | Hill et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2009/0319038 A1 | 12/2009 | Gurskis et al. |
| 2010/0016958 A1 | 1/2010 | St. Goar et al. |
| 2010/0023115 A1 | 1/2010 | Robaina et al. |
| 2010/0023117 A1 | 1/2010 | Yoganathan et al. |
| 2010/0030330 A1 | 2/2010 | Bobo et al. |
| 2010/0049313 A1 | 2/2010 | Alon et al. |
| 2010/0076376 A1 | 3/2010 | Manasse et al. |
| 2010/0076548 A1 | 3/2010 | Konno |
| 2010/0082094 A1 | 4/2010 | Quadri et al. |
| 2010/0094411 A1 | 4/2010 | Tuval et al. |
| 2010/0121436 A1 | 5/2010 | Tuval et al. |
| 2010/0185275 A1 | 7/2010 | Richter et al. |
| 2010/0217382 A1 | 8/2010 | Chau et al. |
| 2010/0249915 A1 | 9/2010 | Zhang |
| 2010/0249923 A1 | 9/2010 | Alkhatib et al. |
| 2010/0298929 A1 | 11/2010 | Thornton et al. |
| 2010/0298931 A1 | 11/2010 | Quadri et al. |
| 2010/0312333 A1 | 12/2010 | Navia et al. |
| 2010/0324554 A1 | 12/2010 | Gifford et al. |
| 2011/0004296 A1 | 1/2011 | Lutter et al. |
| 2011/0015722 A1 | 1/2011 | Hauser et al. |
| 2011/0022166 A1 | 1/2011 | Dahlgren et al. |
| 2011/0029071 A1 | 2/2011 | Zlotnick et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0056064 A1 | 3/2011 | Malewicz et al. |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137409 A1 | 6/2011 | Yana et al. |
| 2011/0137410 A1 | 6/2011 | Hacohen |
| 2011/0153008 A1 | 6/2011 | Marchand et al. |
| 2011/0172784 A1 | 7/2011 | Richter et al. |
| 2011/0208293 A1 | 8/2011 | Tabor |
| 2011/0319988 A1 | 12/2011 | Schankereli et al. |
| 2012/0022639 A1 | 1/2012 | Hacohen et al. |
| 2012/0078347 A1 | 3/2012 | Braido et al. |
| 2012/0078360 A1 | 3/2012 | Rafiee |
| 2012/0101571 A1 | 4/2012 | Thambar et al. |
| 2012/0179239 A1 | 7/2012 | Quadri |
| 2012/0179244 A1 | 7/2012 | Schankereli et al. |
| 2012/0203336 A1 | 8/2012 | Annest |
| 2012/0283824 A1 | 11/2012 | Lutter et al. |
| 2012/0303048 A1 | 11/2012 | Manasse |
| 2013/0030418 A1 | 1/2013 | Taft et al. |
| 2013/0123915 A1 | 5/2013 | Giannetti et al. |
| 2013/0172978 A1 | 7/2013 | Vidlund et al. |
| 2013/0190860 A1 | 7/2013 | Sundt, III |
| 2013/0190861 A1 | 7/2013 | Chau et al. |
| 2013/0197630 A1 | 8/2013 | Azarnoush |
| 2013/0226289 A1 | 8/2013 | Shaolian et al. |
| 2013/0226290 A1 | 8/2013 | Yellin et al. |
| 2013/0238089 A1 | 9/2013 | Lichtenstein et al. |
| 2013/0244927 A1 | 9/2013 | Lal et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261741 A1 | 10/2013 | Accola |
| 2013/0268066 A1 | 10/2013 | Rowe |
| 2013/0274870 A1 | 10/2013 | Lombardi et al. |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |
| 2013/0289717 A1 | 10/2013 | Solem |
| 2013/0289718 A1 | 10/2013 | Tsukashima et al. |
| 2013/0296851 A1 | 11/2013 | Boronyak et al. |
| 2013/0296999 A1 | 11/2013 | Burriesci et al. |
| 2013/0304180 A1 | 11/2013 | Green et al. |
| 2013/0304181 A1 | 11/2013 | Green et al. |
| 2013/0304197 A1 | 11/2013 | Buchbinder et al. |
| 2013/0304198 A1 | 11/2013 | Solem |
| 2013/0304200 A1 | 11/2013 | McLean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1 | 11/2013 | Morriss et al. |
| 2013/0317603 A1 | 11/2013 | McLean et al. |
| 2013/0325110 A1 | 12/2013 | Khalil et al. |
| 2013/0325114 A1 | 12/2013 | McLean et al. |
| 2013/0331864 A1 | 12/2013 | Jelich et al. |
| 2013/0338684 A1 | 12/2013 | Hausen |
| 2013/0338763 A1 | 12/2013 | Rowe et al. |
| 2013/0338766 A1 | 12/2013 | Hastings et al. |
| 2013/0345797 A1 | 12/2013 | Dahlgren et al. |
| 2013/0345803 A1 | 12/2013 | Bergheim, III |
| 2014/0005778 A1 | 1/2014 | Buchbinder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1 | 1/2014 | Murphy et al. |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0094906 A1 | 4/2014 | Spence et al. |
| 2014/0107775 A1 | 4/2014 | Hjelle et al. |
| 2014/0114404 A1 | 4/2014 | Gammie et al. |
| 2014/0114407 A1 | 4/2014 | Raiamannan |
| 2014/0121763 A1 | 5/2014 | Duffy et al. |
| 2014/0128965 A1 | 5/2014 | Rafiee |
| 2014/0135913 A1 | 5/2014 | Lichtenstein et al. |
| 2014/0163652 A1 | 6/2014 | Witzel et al. |
| 2014/0163668 A1 | 6/2014 | Rafiee |
| 2014/0172076 A1 | 6/2014 | Jonsson et al. |
| 2014/0172084 A1 | 6/2014 | Callas et al. |
| 2014/0172085 A1 | 6/2014 | Quadri et al. |
| 2014/0172086 A1 | 6/2014 | Quadri et al. |
| 2014/0179993 A1 | 6/2014 | Alexander et al. |

(56) References Cited

U.S. PATENT DOCUMENTS

| | | |
|---|---|---|
| 2014/0180401 A1 | 6/2014 | Quill et al. |
| 2014/0188108 A1 | 7/2014 | Goodine et al. |
| 2014/0188215 A1 | 7/2014 | Hlavka et al. |
| 2014/0194920 A1 | 7/2014 | Krahbichler |
| 2014/0194976 A1 | 7/2014 | Starksen et al. |
| 2014/0200397 A1 | 7/2014 | Raman et al. |
| 2014/0200649 A1 | 7/2014 | Essinger et al. |
| 2014/0200657 A1 | 7/2014 | Maurer et al. |
| 2014/0200662 A1 | 7/2014 | Eftel et al. |
| 2014/0207011 A1 | 7/2014 | Righini et al. |
| 2014/0214159 A1 | 7/2014 | Vidlund et al. |
| 2014/0219524 A1 | 8/2014 | Takeguchi et al. |
| 2014/0222040 A1 | 8/2014 | Park et al. |
| 2014/0243954 A1 | 8/2014 | Shannon |
| 2014/0243964 A1 | 8/2014 | Venkatasubramanian |
| 2014/0249621 A1 | 9/2014 | Eidenschink |
| 2014/0257101 A1 | 9/2014 | Gaudiani |
| 2014/0257466 A1 | 9/2014 | Board et al. |
| 2014/0257467 A1 | 9/2014 | Lane et al. |
| 2014/0257473 A1 | 9/2014 | Rajamannan |
| 2014/0257475 A1 | 9/2014 | Gross et al. |
| 2014/0275757 A1 | 9/2014 | Goodwin et al. |
| 2014/0276395 A1 | 9/2014 | Wilson et al. |
| 2014/0276609 A1 | 9/2014 | Maaee et al. |
| 2014/0276782 A1 | 9/2014 | Paskar |
| 2014/0276971 A1 | 9/2014 | Kovach |
| 2014/0277119 A1 | 9/2014 | Akpinar |
| 2014/0277390 A1 | 9/2014 | Ratz et al. |
| 2014/0277404 A1 | 9/2014 | Wilson et al. |
| 2014/0277405 A1 | 9/2014 | Wilson et al. |
| 2014/0277406 A1 | 9/2014 | Arcidi |
| 2014/0277407 A1 | 9/2014 | Dale et al. |
| 2014/0277408 A1 | 9/2014 | Folan |
| 2014/0277409 A1 | 9/2014 | Bortlein et al. |
| 2014/0277410 A1 | 9/2014 | Bortlein et al. |
| 2014/0277411 A1 | 9/2014 | Bortlein et al. |
| 2014/0277412 A1 | 9/2014 | Bortlein et al. |
| 2014/0277420 A1 | 9/2014 | Migliazza et al. |
| 2014/0277422 A1 | 9/2014 | Ratz et al. |
| 2014/0288480 A1 | 9/2014 | Zimmerman et al. |
| 2014/0296878 A1 | 10/2014 | Oz et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296975 A1 | 10/2014 | Tegels et al. |
| 2014/0303719 A1 | 10/2014 | Cox et al. |
| 2014/0303721 A1 | 10/2014 | Fung et al. |
| 2014/0309727 A1 | 10/2014 | Lamelas et al. |
| 2014/0309730 A1 | 10/2014 | Alon et al. |
| 2014/0309731 A1 | 10/2014 | Quadri et al. |
| 2014/0309732 A1 | 10/2014 | Solem |
| 2014/0316516 A1 | 10/2014 | Vidlund et al. |
| 2014/0324164 A1 | 10/2014 | Gross et al. |
| 2014/0358222 A1 | 12/2014 | Gorman, III et al. |
| 2014/0358224 A1 | 12/2014 | Tegels et al. |
| 2014/0364944 A1 | 12/2014 | Lutter et al. |
| 2014/0371843 A1 | 12/2014 | Wilson et al. |
| 2014/0371844 A1 | 12/2014 | Dale et al. |
| 2014/0371846 A1 | 12/2014 | Wilson et al. |
| 2014/0379074 A1 | 12/2014 | Spence et al. |
| 2014/0379076 A1 | 12/2014 | Vidlund et al. |
| 2015/0005874 A1 | 1/2015 | Vidlund et al. |
| 2015/0005875 A1 | 1/2015 | Tuval et al. |
| 2015/0025623 A1 | 1/2015 | Granada et al. |
| 2015/0032127 A1 | 1/2015 | Gammie et al. |
| 2015/0045878 A1 | 2/2015 | Rowe |
| 2015/0066140 A1 | 3/2015 | Quadri et al. |
| 2015/0094802 A1 | 4/2015 | Buchbinder et al. |
| 2015/0094803 A1 | 4/2015 | Navia |
| 2015/0100116 A1 | 4/2015 | Mohl et al. |
| 2015/0112427 A1 | 4/2015 | Schweich, Jr. et al. |
| 2015/0112429 A1 | 4/2015 | Khairkhahan et al. |
| 2015/0112433 A1 | 4/2015 | Schweich, Jr. et al. |
| 2015/0119978 A1 | 4/2015 | Tegels et al. |
| 2015/0119981 A1 | 4/2015 | Khairkhahan et al. |
| 2015/0119982 A1 | 4/2015 | Quill et al. |
| 2015/0127091 A1 | 5/2015 | Cecere et al. |
| 2015/0127096 A1 | 5/2015 | Rowe et al. |
| 2015/0142101 A1 | 5/2015 | Coleman et al. |
| 2015/0142103 A1 | 5/2015 | Vidlund |
| 2015/0142105 A1 | 5/2015 | Bolling et al. |
| 2015/0150678 A1 | 6/2015 | Brecker |
| 2015/0157458 A1 | 6/2015 | Thambar et al. |
| 2015/0157459 A1 | 6/2015 | Macoviak et al. |
| 2015/0164637 A1 | 6/2015 | Khairkhahan et al. |
| 2015/0164641 A1 | 6/2015 | Annest |
| 2015/0173897 A1 | 6/2015 | Raanani et al. |
| 2015/0173898 A1 | 6/2015 | Drasler et al. |
| 2015/0173900 A1 | 6/2015 | Hauser et al. |
| 2015/0190229 A1 | 7/2015 | Seguin |
| 2015/0196390 A1 | 7/2015 | Ma et al. |
| 2015/0196393 A1 | 7/2015 | Vidlund et al. |
| 2015/0202043 A1 | 7/2015 | Zakai et al. |
| 2015/0209137 A1 | 7/2015 | Quadri et al. |
| 2015/0209139 A1 | 7/2015 | Granada et al. |
| 2015/0216655 A1 | 8/2015 | Lane et al. |
| 2015/0216661 A1 | 8/2015 | Hacohen et al. |
| 2015/0223802 A1 | 8/2015 | Tegzes |
| 2015/0223934 A1 | 8/2015 | Vidlund et al. |
| 2015/0223935 A1 | 8/2015 | Subramanian et al. |
| 2015/0230920 A1 | 8/2015 | Alfieri et al. |
| 2015/0230921 A1 | 8/2015 | Chau et al. |
| 2015/0238312 A1 | 8/2015 | Lashinski |
| 2015/0238313 A1 | 8/2015 | Spence et al. |
| 2015/0250590 A1 | 9/2015 | Gries et al. |
| 2015/0257877 A1 | 9/2015 | Hernandez |
| 2015/0257878 A1 | 9/2015 | Lane et al. |
| 2015/0257879 A1 | 9/2015 | Bortlein et al. |
| 2015/0257881 A1 | 9/2015 | Bortlein et al. |
| 2015/0257882 A1 | 9/2015 | Bortlein et al. |
| 2015/0272737 A1 | 10/2015 | Dale et al. |
| 2015/0305861 A1 | 10/2015 | Annest |
| 2015/0305864 A1 | 10/2015 | Quadri et al. |
| 2015/0313739 A1 | 11/2015 | Hummen et al. |
| 2015/0320553 A1 | 11/2015 | Chau et al. |
| 2015/0327999 A1 | 11/2015 | Board et al. |
| 2015/0328000 A1 | 11/2015 | Ratz et al. |
| 2015/0336150 A1* | 11/2015 | Peterson ............... B21D 37/00 72/372 |
| 2015/0342733 A1 | 12/2015 | Alkhatib et al. |
| 2015/0351906 A1 | 12/2015 | Hammer et al. |
| 2015/0351908 A1 | 12/2015 | Keranen et al. |
| 2015/0359628 A1 | 12/2015 | Keranen |
| 2015/0359629 A1 | 12/2015 | Ganesan et al. |
| 2015/0359631 A1 | 12/2015 | Sheahan et al. |
| 2015/0366666 A1 | 12/2015 | Khairkhahan et al. |
| 2015/0374495 A1 | 12/2015 | Ruyra Baliarda et al. |
| 2016/0000983 A1 | 1/2016 | Mohl et al. |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0015543 A1 | 1/2016 | Perouse et al. |
| 2016/0030171 A1 | 2/2016 | Quijano et al. |
| 2016/0038246 A1 | 2/2016 | Wang et al. |
| 2016/0038280 A1 | 2/2016 | Morriss et al. |
| 2016/0038283 A1 | 2/2016 | Divekar et al. |
| 2016/0038286 A1 | 2/2016 | Yellin et al. |
| 2016/0074160 A1 | 3/2016 | Christianson et al. |
| 2016/0106539 A1 | 4/2016 | Buchbinder et al. |
| 2016/0113764 A1 | 4/2016 | Sheahan et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120643 A1 | 5/2016 | Kupumbati |
| 2016/0143730 A1 | 5/2016 | Kheradvar |
| 2016/0151154 A1 | 6/2016 | Gorman, III et al. |
| 2016/0151156 A1 | 6/2016 | Seguin et al. |
| 2016/0151552 A1 | 6/2016 | Solem |
| 2016/0157999 A1 | 6/2016 | Lane et al. |
| 2016/0158000 A1 | 6/2016 | Granada et al. |
| 2016/0158001 A1 | 6/2016 | Wallace et al. |
| 2016/0158002 A1 | 6/2016 | Wallace et al. |
| 2016/0158003 A1 | 6/2016 | Wallace et al. |
| 2016/0158415 A1 | 6/2016 | Strasly et al. |

(56) References Cited

U.S. PATENT DOCUMENTS

| | | |
|---|---|---|
| 2016/0184095 A1 | 6/2016 | Spence et al. |
| 2016/0206280 A1 | 7/2016 | Vidlund et al. |
| 2016/0206424 A1 | 7/2016 | Al-Jilaihawi et al. |
| 2016/0262881 A1 | 9/2016 | Schankereli et al. |
| 2016/0317290 A1 | 11/2016 | Chau et al. |
| 2017/0079790 A1 | 3/2017 | Vidlund et al. |
| 2017/0100248 A1 | 4/2017 | Tegels et al. |
| 2017/0100250 A1 | 4/2017 | Marsot et al. |
| 2017/0119526 A1 | 5/2017 | Luong et al. |
| 2017/0128198 A1 | 5/2017 | Cartledge et al. |
| 2017/0128205 A1 | 5/2017 | Tamir et al. |
| 2017/0128206 A1 | 5/2017 | Rafiee et al. |
| 2017/0128208 A1 | 5/2017 | Christianson et al. |
| 2017/0156860 A1 | 6/2017 | Lashinski |
| 2017/0165054 A1 | 6/2017 | Benson et al. |
| 2017/0165055 A1 | 6/2017 | Hauser et al. |
| 2017/0165064 A1 | 6/2017 | Nyuli et al. |
| 2017/0172737 A1 | 6/2017 | Kuetting et al. |
| 2017/0181851 A1 | 6/2017 | Annest |
| 2017/0189177 A1 | 7/2017 | Schweich, Jr. et al. |
| 2017/0189179 A1 | 7/2017 | Ratz et al. |
| 2017/0189180 A1 | 7/2017 | Alkhatib |
| 2017/0189181 A1 | 7/2017 | Alkhatib et al. |
| 2017/0196688 A1 | 7/2017 | Christianson et al. |
| 2017/0231762 A1 | 8/2017 | Quadri et al. |
| 2017/0231763 A1 | 8/2017 | Yellin et al. |
| 2017/0258585 A1 | 9/2017 | Marquez et al. |
| 2017/0266001 A1 | 9/2017 | Vidlund et al. |
| 2017/0281345 A1 | 10/2017 | Yang et al. |
| 2017/0290659 A1 | 10/2017 | Ulmer et al. |
| 2017/0296338 A1 | 10/2017 | Cambell et al. |
| 2017/0296339 A1 | 10/2017 | Thambar et al. |
| 2017/0319333 A1 | 11/2017 | Tegels et al. |
| 2017/0325842 A1 | 11/2017 | Siegel |
| 2017/0325941 A1 | 11/2017 | Wallace et al. |
| 2017/0325945 A1 | 11/2017 | Dale et al. |
| 2017/0325948 A1 | 11/2017 | Wallace et al. |
| 2017/0325949 A1 | 11/2017 | Rodgers et al. |
| 2017/0325953 A1 | 11/2017 | Klima et al. |
| 2017/0325954 A1 | 11/2017 | Perszyk |
| 2017/0333186 A1 | 11/2017 | Spargias |
| 2017/0333188 A1 | 11/2017 | Carpentier et al. |
| 2017/0340440 A1 | 11/2017 | Ratz et al. |
| 2017/0348098 A1 | 12/2017 | Rowe et al. |
| 2017/0348100 A1 | 12/2017 | Lane et al. |
| 2017/0354496 A1 | 12/2017 | Quadri et al. |
| 2017/0354497 A1 | 12/2017 | Quadri et al. |
| 2017/0354499 A1 | 12/2017 | Granada et al. |
| 2017/0360426 A1 | 12/2017 | Hacohen et al. |
| 2017/0360549 A1 | 12/2017 | Lashinski et al. |
| 2017/0360558 A1 | 12/2017 | Ma |
| 2017/0360585 A1 | 12/2017 | White |
| 2017/0367858 A1 | 12/2017 | Saar et al. |
| 2018/0161585 A1 | 6/2018 | Ollivier |
| 2018/0214263 A1 | 8/2018 | Rolando et al. |
| 2018/0221147 A1 | 8/2018 | Ganesan et al. |
| 2018/0235753 A1 | 8/2018 | Ganesan et al. |
| 2018/0296325 A1 | 10/2018 | McLean |
| 2018/0338832 A1 | 11/2018 | Ganesan et al. |
| 2019/0000618 A1 | 1/2019 | Schweich, Jr. et al. |
| 2019/0029814 A1 | 1/2019 | Schweich, Jr. et al. |
| 2019/0142581 A1 | 5/2019 | Maiso et al. |
| 2019/0183641 A1 | 6/2019 | Ganesan et al. |
| 2019/0192292 A1 | 6/2019 | Schweich, Jr. et al. |

FOREIGN PATENT DOCUMENTS

| | | |
|---|---|---|
| CN | 101291637 A | 10/2008 |
| CN | 103491900 A | 1/2014 |
| DE | 19605042 A1 | 1/1998 |
| DE | 102006052564 B3 | 12/2007 |
| EP | 186104 A2 | 7/1986 |
| EP | 0224080 B1 | 7/1992 |
| EP | 1512383 A2 | 3/2005 |
| EP | 1088529 B1 | 6/2005 |
| EP | 1545371 A2 | 6/2005 |
| EP | 1551274 A2 | 7/2005 |
| EP | 1629794 A2 | 3/2006 |
| EP | 1646332 A2 | 4/2006 |
| EP | 170224 7 A2 | 9/2006 |
| EP | 1734903 A1 | 12/2006 |
| EP | 1891914 | 2/2008 |
| EP | 1967164 A2 | 9/2008 |
| EP | 2026280 A1 | 2/2009 |
| EP | 2033581 A1 | 3/2009 |
| EP | 2037829 A2 | 3/2009 |
| EP | 2081519 A2 | 7/2009 |
| EP | 2111190 A2 | 10/2009 |
| EP | 2142143 A2 | 1/2010 |
| EP | 2167742 A1 | 3/2010 |
| EP | 2014257 B1 | 9/2010 |
| EP | 2278944 A2 | 2/2011 |
| EP | 2033597 B1 | 3/2011 |
| EP | 2306821 A1 | 4/2011 |
| EP | 2327429 A1 | 6/2011 |
| EP | 2165651 B1 | 8/2011 |
| EP | 1719476 B1 | 11/2011 |
| EP | 2399527 A1 | 12/2011 |
| EP | 2400924 | 1/2012 |
| EP | 2400926 A2 | 1/2012 |
| EP | 2410947 A1 | 2/2012 |
| EP | 2416739 A2 | 2/2012 |
| EP | 2419050 | 2/2012 |
| EP | 2399527 A8 | 3/2012 |
| EP | 2444031 A2 | 4/2012 |
| EP | 2488126 A1 | 8/2012 |
| EP | 2509538 A2 | 10/2012 |
| EP | 2549955 A1 | 1/2013 |
| EP | 2549956 A1 | 1/2013 |
| EP | 2566416 A1 | 3/2013 |
| EP | 2586492 A1 | 5/2013 |
| EP | 2618784 A2 | 7/2013 |
| EP | 2623068 A1 | 8/2013 |
| EP | 2626013 A2 | 8/2013 |
| EP | 2629699 A1 | 8/2013 |
| EP | 2641 S69 A1 | 9/2013 |
| EP | 26334S7 A1 | 9/2013 |
| EP | 26376S9 A1 | 9/2013 |
| EP | 26S679S A1 | 10/2013 |
| EP | 26S4624 A1 | 10/2013 |
| EP | 26S6794 A1 | 10/2013 |
| EP | 26S6796 A1 | 10/2013 |
| EP | 2644158 | 10/2013 |
| EP | 26703S8 A2 | 12/2013 |
| EP | 2667823 A1 | 12/2013 |
| EP | 2676640 A1 | 12/2013 |
| EP | 2688041 A2 | 1/2014 |
| EP | 2695586 | 2/2014 |
| EP | 2697721 A2 | 2/2014 |
| EP | 2713953 A1 | 4/2014 |
| EP | 2714068 A2 | 4/2014 |
| EP | 2723272 A2 | 4/2014 |
| EP | 2723273 A2 | 4/2014 |
| EP | 2723277 A1 | 4/2014 |
| EP | 2739214 A2 | 6/2014 |
| EP | 2741711 A2 | 6/2014 |
| EP | 2750630 A1 | 7/2014 |
| EP | 2750631 A1 | 7/2014 |
| EP | 2755562 A1 | 7/2014 |
| EP | 2755602 A1 | 7/2014 |
| EP | 2757962 A1 | 7/2014 |
| EP | 2777616 A1 | 9/2014 |
| EP | 2777617 A1 | 9/2014 |
| EP | 2782523 A1 | 10/2014 |
| EP | 2785282 A1 | 10/2014 |
| EP | 2786817 | 10/2014 |
| EP | 2790609 A1 | 10/2014 |
| EP | 2793751 A1 | 10/2014 |
| EP | 2229921 B1 | 11/2014 |
| EP | 2S1442S A1 | 12/2014 |
| EP | 2S09263 A2 | 12/2014 |
| EP | 2S10620 A1 | 12/2014 |
| EP | 2S14429 A1 | 12/2014 |
| EP | 2S19617 A1 | 1/2015 |

(56) References Cited

FOREIGN PATENT DOCUMENTS

| | | |
|---|---|---|
| EP | 2819618 A1 | 1/2015 |
| EP | 2819619 A1 | 1/2015 |
| EP | 2838475 A1 | 2/2015 |
| EP | 2717803 | 2/2015 |
| EP | 2833836 A1 | 2/2015 |
| EP | 2839815 | 2/2015 |
| EP | 2844190 | 3/2015 |
| EP | 2849680 A2 | 3/2015 |
| EP | 2849681 A1 | 3/2015 |
| EP | 2852354 A2 | 4/2015 |
| EP | 2854719 | 4/2015 |
| EP | 2861186 A2 | 4/2015 |
| EP | 2870933 | 5/2015 |
| EP | 2873011 A1 | 5/2015 |
| EP | 2875797 A | 5/2015 |
| EP | 2760375 | 6/2015 |
| EP | 2882374 A1 | 6/2015 |
| EP | 2886082 | 6/2015 |
| EP | 2886083 A1 | 6/2015 |
| EP | 2886084 A1 | 6/2015 |
| EP | 2895111 A2 | 7/2015 |
| EP | 2250976 B1 | 8/2015 |
| EP | 2901966 A1 | 8/2015 |
| EP | 2907479 A1 | 8/2015 |
| EP | 2945572 A1 | 11/2015 |
| EP | 2948094 A1 | 12/2015 |
| EP | 2948102 A1 | 12/2015 |
| EP | 2968847 A1 | 1/2016 |
| EP | 2964152 A1 | 1/2016 |
| EP | 2967859 A1 | 1/2016 |
| EP | 2967860 A1 | 1/2016 |
| EP | 2967866 A2 | 1/2016 |
| EP | 2981208 | 2/2016 |
| EP | 2982336 A1 | 2/2016 |
| EP | 2999433 A1 | 3/2016 |
| EP | 3003187 A1 | 4/2016 |
| EP | 3003219 A1 | 4/2016 |
| EP | 3003220 A1 | 4/2016 |
| EP | 3010447 A1 | 4/2016 |
| EP | 3013281 A1 | 5/2016 |
| EP | 3017792 A1 | 5/2016 |
| EP | 3021792 A2 | 5/2016 |
| EP | 3023117 A1 | 5/2016 |
| EP | 3027143 A1 | 6/2016 |
| EP | 3033048 A2 | 6/2016 |
| EP | 3037064 A1 | 6/2016 |
| EP | 3050541 A1 | 8/2016 |
| EP | 3079633 | 10/2016 |
| EP | 3229736 | 11/2016 |
| EP | 3102152 A1 | 12/2016 |
| EP | 2470119 B1 | 5/2017 |
| EP | 2999436 M | 5/2017 |
| EP | 3184081 | 6/2017 |
| EP | 3191027 | 7/2017 |
| EP | 2611389 | 8/2017 |
| EP | 3082656 | 8/2017 |
| EP | 3206628 | 8/2017 |
| EP | 2010103 | 9/2017 |
| EP | 2509538 B1 | 9/2017 |
| EP | 3223751 | 10/2017 |
| EP | 3027144 | 11/2017 |
| EP | 3110368 | 11/2017 |
| EP | 3110369 | 11/2017 |
| EP | 3132773 | 11/2017 |
| EP | 3245980 | 11/2017 |
| EP | 3250154 | 12/2017 |
| EP | 3256077 | 12/2017 |
| EP | 3258883 | 12/2017 |
| EP | 3273910 | 1/2018 |
| JP | 6504516 | 5/1994 |
| JP | H10258124 A | 9/1998 |
| JP | 2002509756 A | 4/2002 |
| JP | 2005280917 A | 10/2005 |
| JP | 2008528117 A | 7/2008 |
| JP | 2008541863 A | 11/2008 |
| JP | 2009195712 A | 9/2009 |
| JP | 2010518947 A | 6/2010 |
| JP | 5219518 B2 | 6/2013 |
| WO | WO-1992017118 A1 | 10/1992 |
| WO | WO-1995016407 A1 | 6/1995 |
| WO | WO-1999004730 A1 | 2/1999 |
| WO | WO-1999039648 A1 | 8/1999 |
| WO | WO-1999049799 A1 | 10/1999 |
| WO | WO-2001010343 | 2/2001 |
| WO | WO-2002003892 A1 | 1/2002 |
| WO | WO-2002028421 A1 | 4/2002 |
| WO | WO-2002039908 A2 | 5/2002 |
| WO | WO-2003043685 A2 | 5/2003 |
| WO | WO-2004084746 A2 | 10/2004 |
| WO | WO-2004093728 A2 | 11/2004 |
| WO | WO-2004096097 A2 | 11/2004 |
| WO | WO-2004112657 A1 | 12/2004 |
| WO | WO-2005002466 A2 | 1/2005 |
| WO | WO-2005007219 A2 | 1/2005 |
| WO | WO-2005009285 A2 | 2/2005 |
| WO | WO-2005009506 A2 | 2/2005 |
| WO | WO-2005087140 A1 | 9/2005 |
| WO | WO-2006041877 A2 | 4/2006 |
| WO | WO-2006063199 A2 | 6/2006 |
| WO | WO-2007008371 A1 | 1/2007 |
| WO | WO-2007067820 A2 | 6/2007 |
| WO | WO2007098232 | 8/2007 |
| WO | WO-2008022077 A2 | 2/2008 |
| WO | WO-2008035337 A2 | 3/2008 |
| WO | WO-2008028569 A1 | 3/2008 |
| WO | 2008103722 | 8/2008 |
| WO | WO-2008103497 A2 | 8/2008 |
| WO | WO-2008129405 A2 | 10/2008 |
| WO | WO-2009045338 A1 | 4/2009 |
| WO | 2009091509 | 7/2009 |
| WO | WO-2010006627 A1 | 1/2010 |
| WO | WO-2010008549 A1 | 1/2010 |
| WO | WO-2010057262 A1 | 5/2010 |
| WO | WO-2010080594 A2 | 7/2010 |
| WO | WO-2010098857 A1 | 9/2010 |
| WO | WO-2010099032 A2 | 9/2010 |
| WO | 2010121076 | 10/2010 |
| WO | WO-2010117680 A1 | 10/2010 |
| WO | 2011025981 | 3/2011 |
| WO | WO-2011047168 A1 | 4/2011 |
| WO | WO-2011051043 A1 | 5/2011 |
| WO | WO-2011057087 A1 | 5/2011 |
| WO | WO-2011072084 A2 | 6/2011 |
| WO | WO-2011106137 A1 | 9/2011 |
| WO | WO-2011106544 A1 | 9/2011 |
| WO | WO-2011111047 A2 | 9/2011 |
| WO | WO-2011137531 A1 | 11/2011 |
| WO | WO-2011139747 A1 | 11/2011 |
| WO | WO-2012011108 A2 | 1/2012 |
| WO | WO-2012011018 A1 | 1/2012 |
| WO | WO-2012027487 A2 | 3/2012 |
| WO | WO-2012035279 A1 | 3/2012 |
| WO | WO-2012040655 A2 | 3/2012 |
| WO | 2012052718 | 4/2012 |
| WO | WO-2012047644 A2 | 4/2012 |
| WO | WO-2012055498 A1 | 5/2012 |
| WO | WO-2012087842 A1 | 6/2012 |
| WO | WO-2012095455 A2 | 7/2012 |
| WO | WO-2012102928 A1 | 8/2012 |
| WO | WO-2012106602 A2 | 8/2012 |
| WO | WO-2012118508 A1 | 9/2012 |
| WO | WO-2012118816 A1 | 9/2012 |
| WO | WO-2012118894 A2 | 9/2012 |
| WO | WO-2012177942 A2 | 12/2012 |
| WO | WO-2013021374 A2 | 2/2013 |
| WO | WO-2013021375 A2 | 2/2013 |
| WO | WO-2013028387 A2 | 2/2013 |
| WO | WO-2013059743 A1 | 4/2013 |
| WO | WO-2013059747 A1 | 4/2013 |
| WO | WO-2013114214 A2 | 8/2013 |
| WO | WO-2013120181 A1 | 8/2013 |
| WO | WO-2013123059 A1 | 8/2013 |
| WO | WO-2013128432 A1 | 9/2013 |
| WO | WO-2013130641 A1 | 9/2013 |

(56) References Cited

FOREIGN PATENT DOCUMENTS

| | | |
|---|---|---|
| WO | WO-2013131925 A1 | 9/2013 |
| WO | WO-2013140318 A1 | 9/2013 |
| WO | WO-2013148017 A1 | 10/2013 |
| WO | WO-2013148018 A1 | 10/2013 |
| WO | WO-2013148019 A1 | 10/2013 |
| WO | WO-2013150512 A1 | 10/2013 |
| WO | WO-2013152161 A1 | 10/2013 |
| WO | WO-2013158613 A1 | 10/2013 |
| WO | WO-2013169448 A1 | 11/2013 |
| WO | WO-2013175468 A2 | 11/2013 |
| WO | WO-2013176583 A2 | 11/2013 |
| WO | WO-2013188077 A1 | 12/2013 |
| WO | WO-2013192107 A1 | 12/2013 |
| WO | WO-201404 7325 A1 | 3/2014 |
| WO | WO-2014036113 A1 | 3/2014 |
| WO | WO-2014043527 A2 | 3/2014 |
| WO | WO-2014047111 A1 | 3/2014 |
| WO | WO-2014055981 A1 | 4/2014 |
| WO | WO-2014059432 A2 | 4/2014 |
| WO | WO-2014064694 A2 | 5/2014 |
| WO | WO-2014066365 A1 | 5/2014 |
| WO | WO-2014089424 A1 | 6/2014 |
| WO | WO-2014093861 A1 | 6/2014 |
| WO | WO-2014114 794 A2 | 7/2014 |
| WO | WO-2014111918 A1 | 7/2014 |
| WO | WO-2014114795 A1 | 7/2014 |
| WO | WO-2014114796 A1 | 7/2014 |
| WO | WO-2014114798 A1 | 7/2014 |
| WO | WO-2014116502 A1 | 7/2014 |
| WO | WO-2014121280 A2 | 8/2014 |
| WO | WO-2014128705 A1 | 8/2014 |
| WO | WO-2014144100 A2 | 9/2014 |
| WO | WO-2014134277 A1 | 9/2014 |
| WO | WO-2014138194 A1 | 9/2014 |
| WO | WO-2014138284 A1 | 9/2014 |
| WO | WO-2014138482 A1 | 9/2014 |
| WO | WO-2014138868 A1 | 9/2014 |
| WO | WO-2014144937 A2 | 9/2014 |
| WO | WO-2014145338 A1 | 9/2014 |
| WO | WO-2014147336 A1 | 9/2014 |
| WO | WO-2014152306 A1 | 9/2014 |
| WO | WO-2014152375 A2 | 9/2014 |
| WO | WO-2014152503 A1 | 9/2014 |
| WO | WO-2014153544 A1 | 9/2014 |
| WO | WO-2014155617 A1 | 10/2014 |
| WO | WO-2014162151 A2 | 10/2014 |
| WO | WO-2014162306 A2 | 10/2014 |
| WO | WO-2014163705 A1 | 10/2014 |
| WO | WO-2014168655 A1 | 10/2014 |
| WO | WO-2014179391 A2 | 11/2014 |
| WO | WO-2014181336 A1 | 11/2014 |
| WO | WO-2014189974 A1 | 11/2014 |
| WO | WO-2014210299 A1 | 12/2014 |
| WO | WO-2014191994 A1 | 12/2014 |
| WO | WO-2014194178 A1 | 12/2014 |
| WO | WO-2014201384 A1 | 12/2014 |
| WO | WO-2014201452 A1 | 12/2014 |
| WO | WO-2014205064 A1 | 12/2014 |
| WO | WO-2014207699 A1 | 12/2014 |
| WO | WO-2014210124 A1 | 12/2014 |
| WO | WO-2015009503 A2 | 1/2015 |
| WO | WO-2015020971 A1 | 2/2015 |
| WO | WO-2015028986 A1 | 3/2015 |
| WO | WO-201505 7735 A1 | 4/2015 |
| WO | WO-2015051430 A1 | 4/2015 |
| WO | WO-2015052663 A1 | 4/2015 |
| WO | WO-2015057407 A1 | 4/2015 |
| WO | WO-2015057995 A2 | 4/2015 |
| WO | WO-2015061378 A1 | 4/2015 |
| WO | WO-2015061431 A1 | 4/2015 |
| WO | WO-2015061463 A1 | 4/2015 |
| WO | WO-2015061533 A1 | 4/2015 |
| WO | WO-2015075128 A1 | 5/2015 |
| WO | WO-2015081775 A1 | 6/2015 |
| WO | WO-2015089334 A1 | 6/2015 |
| WO | WO-2015092554 A2 | 6/2015 |
| WO | 2015118464 A1 | 8/2015 |
| WO | WO-2015120122 A2 | 8/2015 |
| WO | WO-2015125024 A2 | 8/2015 |
| WO | WO-2015127264 A1 | 8/2015 |
| WO | WO-2015127283 A1 | 8/2015 |
| WO | WO-2015128739 A2 | 9/2015 |
| WO | WO-2015128741 A2 | 9/2015 |
| WO | WO-2015128747 A2 | 9/2015 |
| WO | WO-2015132667 A1 | 9/2015 |
| WO | WO-2015132668 A1 | 9/2015 |
| WO | WO-2015135050 A1 | 9/2015 |
| WO | WO-2015142648 A1 | 9/2015 |
| WO | WO-2015142834 A1 | 9/2015 |
| WO | WO-2015148241 A1 | 10/2015 |
| WO | 2015179181 | 11/2015 |
| WO | WO-2015171190 A1 | 11/2015 |
| WO | WO-2015171743 A2 | 11/2015 |
| WO | WO-2015191604 | 12/2015 |
| WO | WO-2015191839 A1 | 12/2015 |
| WO | WO-2015195823 A1 | 12/2015 |
| WO | WO-2016011185 A1 | 1/2016 |
| WO | WO-2016020918 A1 | 2/2016 |
| WO | WO-2016027272 A1 | 2/2016 |
| WO | WO-2016059533 A1 | 4/2016 |
| WO | WO-2016065158 A1 | 4/2016 |
| WO | WO-2016073741 A1 | 5/2016 |
| WO | WO-201609733 7 A1 | 6/2016 |
| WO | WO-2016083551 A1 | 6/2016 |
| WO | WO-2016093877 A1 | 6/2016 |
| WO | WO-2016108181 A1 | 7/2016 |
| WO | 2016133950 | 8/2016 |
| WO | WO2016150806 | 9/2016 |
| WO | WO2016201024 | 12/2016 |
| WO | WO2016209970 | 12/2016 |
| WO | WO2017011697 | 1/2017 |
| WO | WO-2017062640 | 4/2017 |
| WO | 2017087701 | 5/2017 |
| WO | 2017096157 | 6/2017 |
| WO | 2017100927 | 6/2017 |
| WO | 2017101232 | 6/2017 |
| WO | 2017117388 | 7/2017 |
| WO | 2017127939 | 8/2017 |
| WO | 2017136287 | 8/2017 |
| WO | 2017136596 | 8/2017 |
| WO | 2017165810 | 9/2017 |
| WO | 2017/173331 A1 | 10/2017 |
| WO | 2017192960 | 11/2017 |
| WO | 2017196511 | 11/2017 |
| WO | 2017196909 | 11/2017 |
| WO | 2017196977 | 11/2017 |
| WO | 2017197064 | 11/2017 |
| WO | 2017197065 | 11/2017 |
| WO | 2017218671 | 12/2017 |
| WO | 2017223486 | 12/2017 |
| WO | 2018017886 | 1/2018 |
| WO | WO2018029680 | 2/2018 |
| WO | 2018/167536 A1 | 9/2018 |
| WO | 2019/069145 A1 | 4/2019 |
| WO | 2019/209927 A1 | 10/2019 |

OTHER PUBLICATIONS

International Search Report and Written Opinion dated Jul. 11, 2018 for PCT Application No. PCT/US2018/027990, 15 pages.
International Search Report and Written Opinion dated Jun. 28, 2018 for PCT Application No. PCT/US2018/027983, 15 pages.
International Search Report and Written Opinion dated Aug. 3, 2018 for PCT Application No. PCT/US2018035086, 15 pages.
International Search Report and Written Opinion dated Aug. 9, 2018 for PCT Application No. PCT/US2018/035081, 11 pages.
International Search Report and Written Opinion dated Sep. 11, 2018 for PCT Application No. PCT/US2018/038841, 15 pages.
International Search Report and Written Opinion dated Sep. 4, 2018 for PCT Application No. PCT/US2018/027966, 17 pages.
International Search Report and Written Opinion dated Sep. 11, 2018 for PCT Application No. PCT/US2018/038847, 18 pages.

(56) References Cited

OTHER PUBLICATIONS

International Search Report and Written Opinion dated Jul. 3, 2018 for PCT Application No. PCT/US2018/031438, 14 pages.
Bernard et al., "Aortic Valve Area Evolution After Percutaneous Aortic Valvuloplasty," European Heart Journal, Jul. 1990, vol. 11 (2), pp. 98-107.
BlueCross BlueShield of Northern Carolina Corporate Medical Policy "Balloon valvuloplasty, Percutaneous", (Jun. 1994).
Cimino et al., "Physics of Ultrasonic Surgery Using Tissue Fragmentation: Part I and Part II", Ultrasound in Medicine and Biology!, Jun. 1996, vol. 22 (1), pp. 89-100, and pp. 101-117.
Cimino, "Ultrasonic Surgery: Power Quantification and Efficiency Optimization", Aesthetic Surgery Journal, Feb. 2001, pp. 233-241.
Cowell et al., "A Randomized Trial of Intensive Lipid-Lowering Therapy in Calcific Aortic Stenosis," NEJM, Jun. 2005, vol. 352 (23), pp. 2389-2397.
De Korte et al., "Characterization of Plaque Components and Vulnerability with Intravascular Ultrasound Elastography", Phys. Med. Biol., Feb. 2000, vol. 45, pp. 1465-1475.
European Search Report dated Mar. 13, 2015 for European Application. No. 05853460.3.
Feldman, "Restenosis Following Successful Balloon Valvuloplasty: Bone Formation in Aortic Valve Leaflets", Cathet Cardiovasc Diagn, May 1993, vol. 29 (1), pp. 1-7.
Fitzgerald et al., "Intravascular Sonotherapy Decreased Neointimal Hyperplasia After Stent Implantation in Swine", Circulation, Feb. 2001, vol. 103, pp. 1828-1831.
Freeman et al., "Ultrasonic Aortic Valve Decalcification: Serial Doppler EchocardiographicFollow Up", J Am Coll Cardiol., Sep. 1990, vol. 16 (3), pp. 623-630.
Greenleaf et al., "Selected Methods for Imaging Elastic Properties of Biological Tissues", Annu. Rev. Biomed. Eng., Apr. 2003, vol. 5, pp. 57-78.
Guzman et al., "Bioeffects Caused by Changes in Acoustic Cavitation Bubble Density and Cell Concentration: A Unified Explanation Based on Cell-to-Bubble Ratio and Blast Radius", Ultrasound in Med. & Biol., Mar. 2003, vol. 29 (8), pp. 1211-1222.
Hallgrimsson et al., "Chronic Non-Rheumatic Aortic Valvular Disease: a Population StudyBased on Autopsies", J Chronic Dis., Jun. 1979, vol. 32 (5), pp. 355-363.
Isner et al., "Contrasting Histoarchitecture of Calcified Leaflets from Stenotic Bicuspid Versus Stenotic Tricuspid Aortic Valves", J Am Coll Cardiol., Apr. 1990, vol. 15 (5), p. 1104-1108.
Lung et al., "A Prospective Survey of Patients with Valvular Heart Disease in Europe: The Euro Heart Survey on Valvular Heart Disease", Euro Heart Journal, Mar. 2003, vol. 24, pp. 1231-1243.
McBride et al "Aortic Valve Decalcification", J Thorac Cardiovas—Surg, Jul. 1990, vol. 100, pp. 36-42.
Miller et al., "Lysis and Sonoporation of Epidermoid and Phagocytic Monolayer Cells by Diagnostic Ultrasound Activation of Contrast Agent Gas Bodies", Ultrasound in Med. & Biol., May 2007, vol. 27 (8), pp. 1107-1113.
Mohler, "Mechanisms of Aortic Valve Calcificaion", Am J Cardiol, Dec. 2004, vol. 94 (11),pp. 1396-1402.
Otto et al., "Three-Year Outcome After Balloon Aortic Valvuloplasty. Insights into Prognosis of Valvular Aortic Stenosis", Circulation, Feb. 1994, vol. 89, pp. 642-650.
Gunn et al., "New Developments in Therapeutic Ultra-sound-Assisted Coronary Angioplasty", Curr Interv Cardiol Rep., Dec. 1990, vol. 1 (4), pp. 281-290.
Passik et al., "Temporal Changes in the Causes of Aortic Stenosis: A Surgical Pathologic Study of 646 Cases", Mayo Clin Proc, Feb. 1987, vol. 62, pp. 19-123.
Quaden et al., "Percutaneous Aortic Valve Replacement: Resection Before Implantation", EurJ Cardiothorac Surg, Jan. 2005, vol. 27, pp. 836-840.
Riebman et al., "New Concepts in the Management of Patients with Aortic Valve Disease", Abstract, Valvular Heart Disease, JACC, Mar. 2004, p. 34A.
Rosenschein et al., "Percutaneous Transluminal Therapy of Occluded Saphenous Vein Grafts" Circulation, Jan. 1999, vol. 99, pp. 26-29.
Sakata et al., "Percutaneous Balloon Aortic Valvuloplasty: Antegrade Transseptal vs. Conventional Retrograde Transarterial Approach", Catheter Cardiovasc Interv., Mar. 2005, vol. 64 (3), pp. 314-321.
Sasaki et al., "Scanning Electron Microscopy and Fourier Transformed Infrared Spectroscopy Analysis of Bone Removal Using Er:YAG and CO2 Lasers", J Periodontal., Jun. 2002, vol. 73 (6), 00. 643-652.
Search Report and Written Opinion dated Dec. 10, 2012 for PCT Application No. PCT/US2012/043636.
Search Report and Written Opinion dated Dec. 6, 2016 for PCT Application No. PCT/US2016/047831.
Search Report and Written Opinion dated Apr. 19, 2014 PCT Application No. PCT/US2012/061215.
Search Report and Written Opinion dated Apr. 19, 2014 PCT Application No. PCT/US2012/061219.
Search Report and Written Opinion dated Mar. 2, 2015 for PCT Application No. PCT/US2014/029549.
Search Report and Written Opinion dated May 1, 2012 for PCT Application No. PCT/US2011/065627.
Search Report and Written Opinion dated May 22, 2007 for PCT Application No. PCT/US2005/044543.
Search Report and Written Opinion dated Oct. 20, 2014 for PCT Application No. PCT/US2014/038849.
Search Report and Written Opinion dated Sep. 4, 2014 for PCT Application No. PCT/US2014/014704.
The CoreValve System Medtronic, 2012, 4 Pages.
Van Den Brand et al., "Histological Changes in the Aortic Valve after Balloon Dilation: Evidence for a Delayed Healing Process", Br Heart J, Jun. 1992, vol. 67, pp. 445-459.
Verdaadadonk et al., "The Mechanism of Action of the Ultrasonic Tissue Resectors Disclosed Using High-Speed and Thermal Imaging Techniques", SPIE, Jan. 1999, vol. 3594, pp. 221-231.
Voelker et al., "Inoperative Valvuloplasty in Calcific Aortic Stenosis: a Study Comparing the Mechanism of a Novel Expandable Device with Conventional Balloon Dilation", Am Heart J., Nov. 1991, vol. 122 (5), pp. 1327-1333.
Waller et al., "Catheter Balloon Valvuloplasty of Stenotic Aortic Valves. Part II: Balloon Valvuloplasty During Life Subsequent Tissue Examination", Clin Cardiol., Nov. 1991, vol. 14 (11), pp. 924-930.
Wang, "Balloon Aortic Valvuloplasty", Prog Cardiovasc Dis., Jul.-Aug. 1997, vol. 40 (1), pp. 27-36.
Wilson et al., "Elastography—The movement Begins", Phys. Med. Biol., Jun. 2000, vol. 45, pp. 1409-1421.
Yock et al, "Catheter-Based Ultrasound Thrombolysis", Circulation, Mar. 1997, vol. 95 (6), pp. 1411-1416.

\* cited by examiner

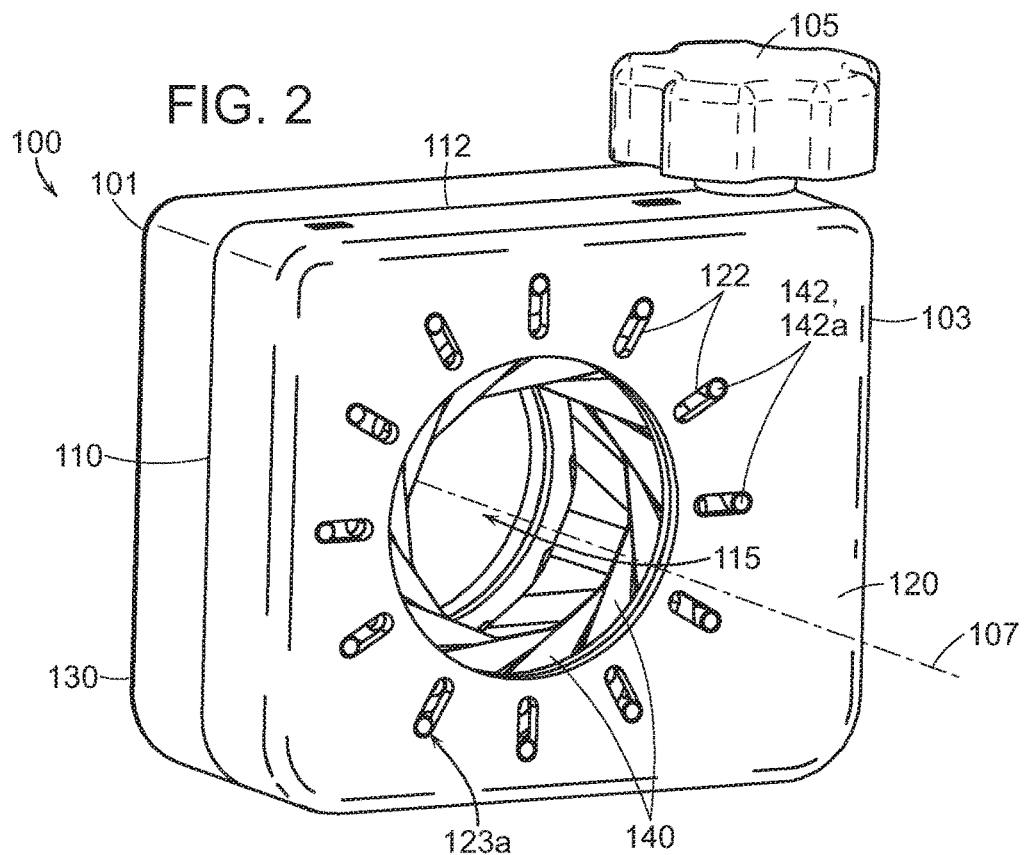
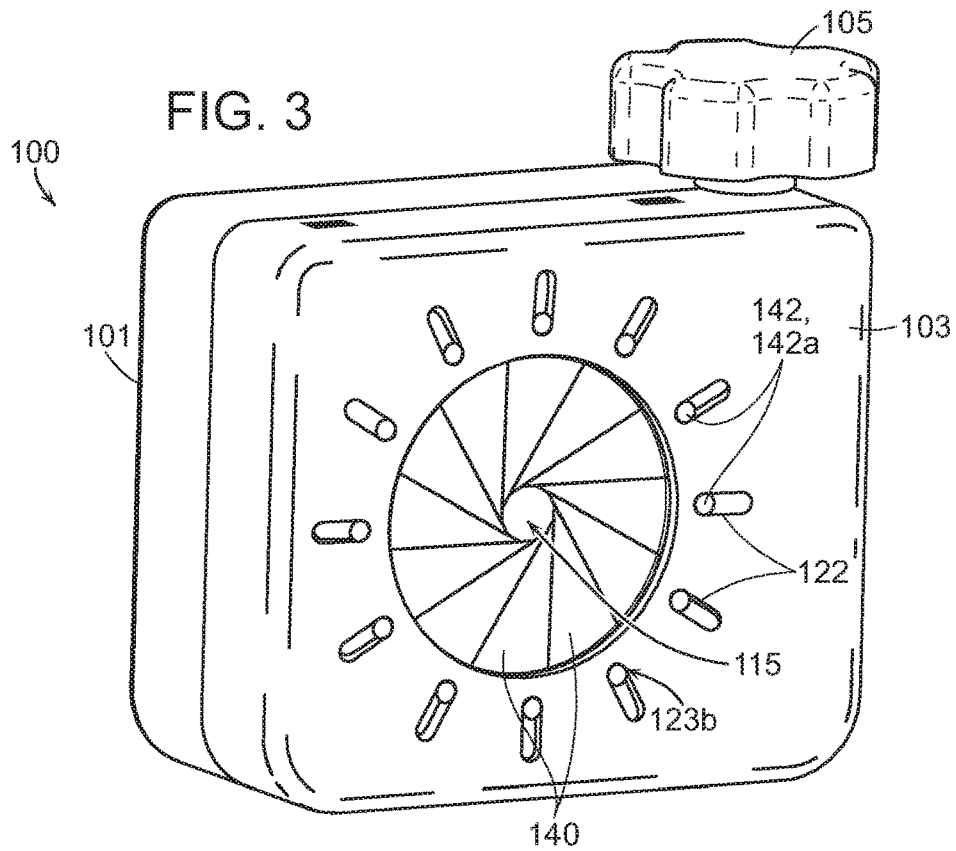

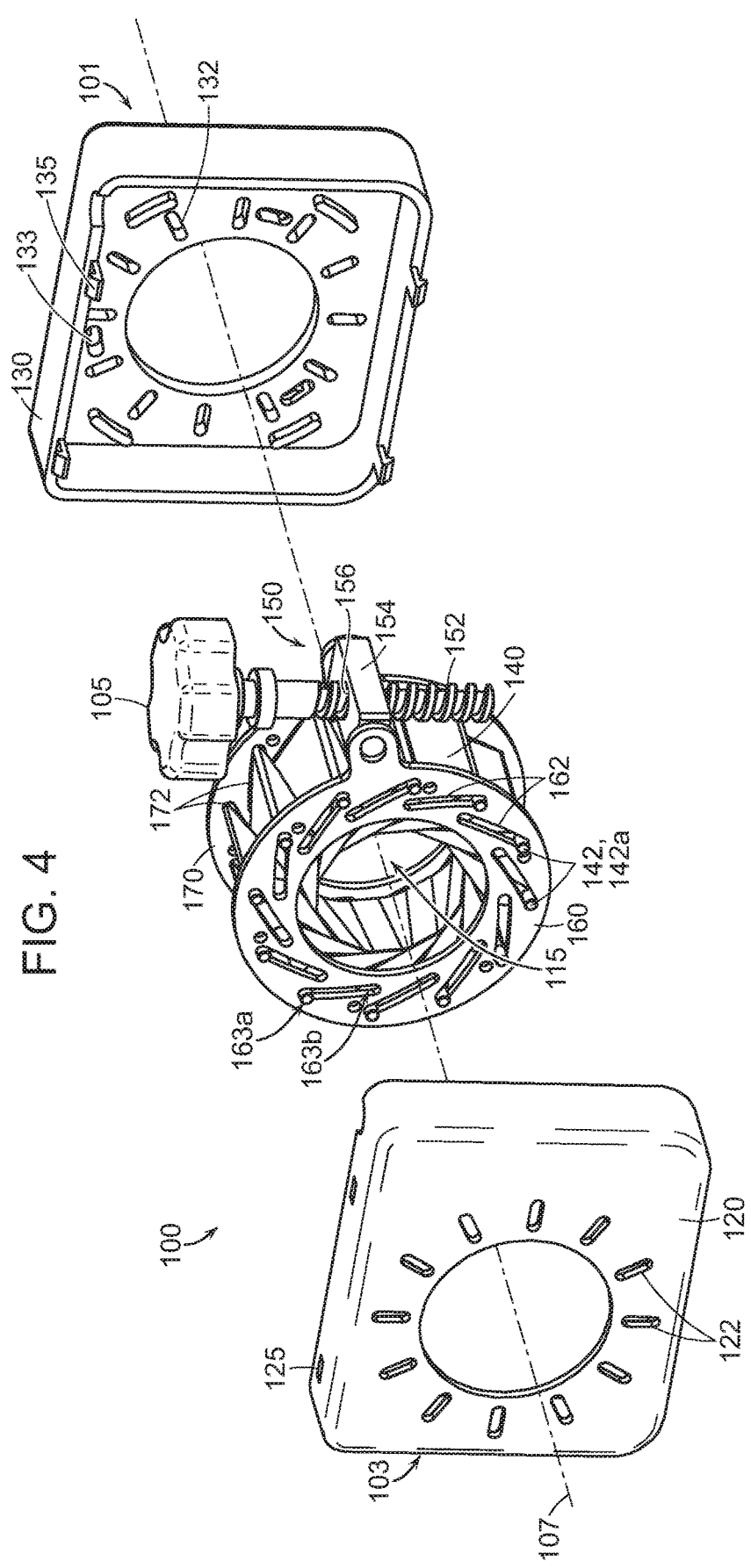

CRIMPING DEVICE FOR LOADING STENTS AND PROSTHETIC HEART VALVES

This application is a continuation of U.S. patent application Ser. No. 15/615,144, filed Jun. 6, 2017, the entire contents of which are incorporated herein by reference.

TECHNICAL FIELD

The present technology relates generally to devices, systems, and methods for reducing the size of a medical device. In particular, some embodiments of the present technology relate to compact crimping devices for reducing a size of prosthetic heart valve devices.

BACKGROUND

Medical devices, such as stents and prosthetic valve devices, can be introduced into a lumen of a body vessel via percutaneous catheterization techniques. These medical devices may be expandable from a first cross-sectional dimension that allows for percutaneous device delivery to a second cross-sectional dimension at a treatment site. In the expanded state, the medical device has a larger cross-sectional dimension than the catheter used to deliver the medical device. Accordingly, a crimping device is typically used to crimp (i.e., reduce) a cross-sectional dimension of the medical device so that the medical device can be loaded into the catheter and advanced to a treatment location in the body. At the treatment location, the medical device can be removed from the catheter and expanded (e.g., via self-expansion, balloon catheter expansion, or mechanical expansion means) to provide a treatment function.

Prosthetic heart valve devices (e.g., prosthetic mitral valve devices) can have a large cross-sectional dimension in the expanded state relative to other medical devices (e.g., stents) delivered via percutaneous catheterization techniques. For example, some prosthetic mitral valves can have an expanded cross sectional dimension of 1.97 inches or more. It is often desirable to package and store prosthetic heart valve devices in their expanded state until just before implantation into the patient. For example, prosthetic heart valve devices can be stored in a sterile solution up until the time the prosthetic heart valve device is ready to be loaded into a delivery system for implantation. Therefore, it is often desirable to crimp prosthetic heart valve devices in the operating room and only a few minutes before a procedure to implant the prosthetic heart valve device. Such procedures preclude pre-crimping by the manufacturer, and benefit from crimping devices that are highly portable and readily available as a sterile system.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. The headings provided herein are for convenience only.

FIGS. 2 and 3 are isometric views of a crimping device of the system of FIG. 1 in a first position and a second position, respectively, in accordance with embodiments of the present technology.

FIG. 4 is a partially exploded view of the crimping device shown in FIGS. 2 and 3.

DETAILED DESCRIPTION

The present technology is generally directed to systems including crimping devices for reducing the size of prosthetic heart valve devices and other medical devices. The term "crimp" (e.g., used in relation to a crimping device or a crimping method) can refer to devices and methods that compact or compress a medical device to a smaller size. Specific details of several embodiments of the present technology are described herein with reference to FIGS. 1-9. Although many of the embodiments are described with respect to devices, systems, and methods for crimping, loading, and delivering prosthetic heart valve devices to a native mitral valve, other applications and other embodiments in addition to those described herein are within the scope of the present technology. For example, at least some embodiments of the present technology may be useful for delivering prosthetics to other native valves, such as the tricuspid valve or the aortic valve. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

With regard to the terms "distal" and "proximal" within this description, unless otherwise specified, the terms can reference relative positions of portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter).

Overview

Figure 1:
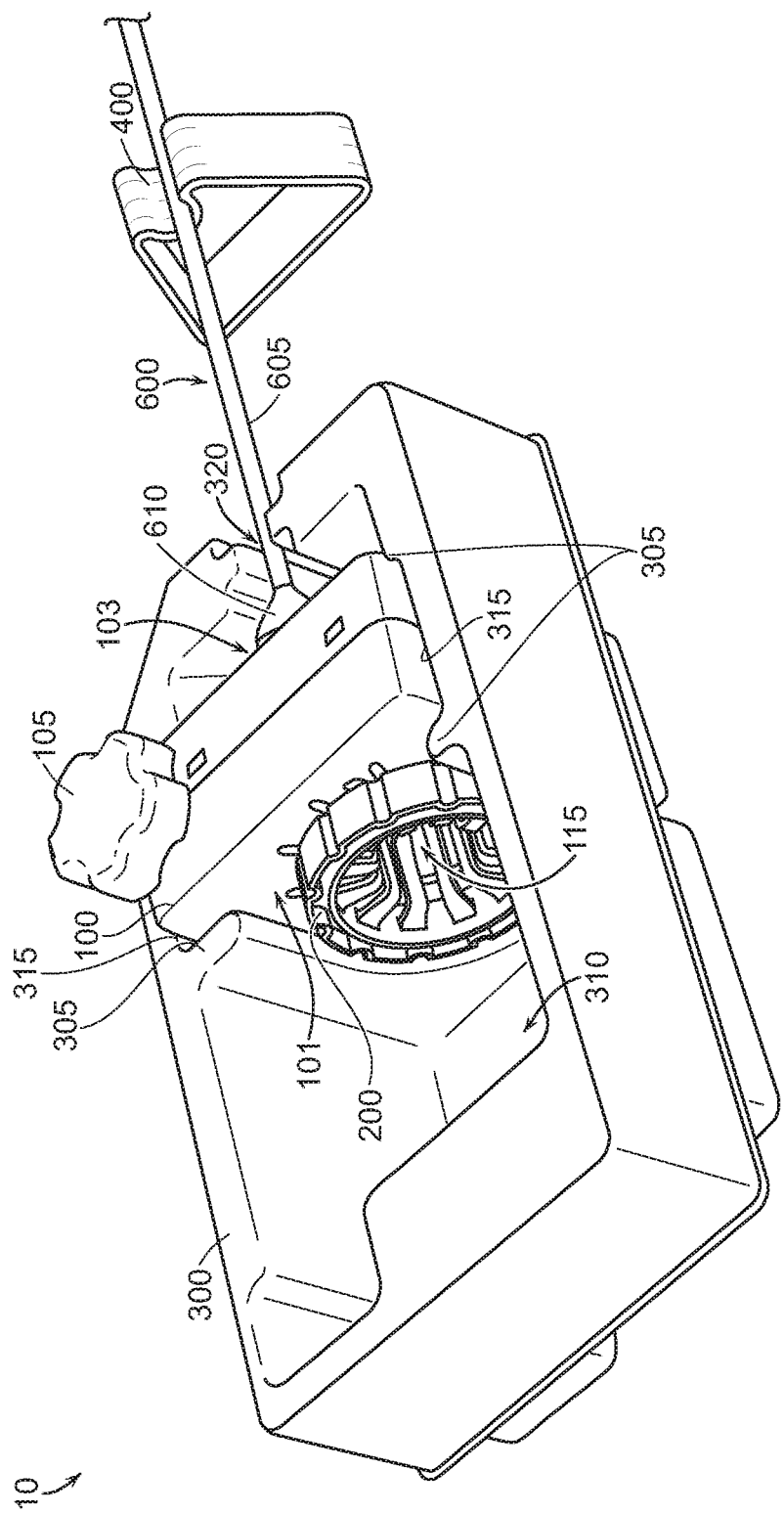
FIG. 1 is an isometric view of a system for reducing the size of a medical device configured in accordance with some embodiments of the present technology.

FIG. 1 shows an embodiment of a crimping and loading system 10 ("system 10") for reducing the size of a medical device in accordance with the present technology. In particular, the system 10 can be used to crimp or compact the medical device to enable the medical device to be loaded into a delivery system for percutaneously delivering the medical device to a patient. In some embodiments, the medical device can be a prosthetic heart valve device. More particularly, the medical device can be a mitral valve device for implantation into a native mitral valve and the delivery system can be a delivery system for delivering the mitral valve device to the native mitral valve, such as one or more of the mitral valve devices and/or delivery systems disclosed in (1) International Patent Application No. PCT/US2014/029549, filed Mar. 14, 2014, (2) International Patent Application No. PCT/US2012/061219, filed Oct. 19, 2012, (3) International Patent Application No. PCT/US2012/061215, filed Oct. 19, 2012, (4) International Patent Application No. PCT/US2012/043636, filed Jun. 21, 2012, (5) U.S. patent application Ser. No. 15/490,047, filed Apr. 18, 2017, and (6) U.S. patent application Ser. No. 15/490,008, filed Apr. 18, 2017, each of which is incorporated herein by reference in its entirety.

As shown in FIG. 1, the system 10 includes a crimping device 100, a medical device holder 200 ("holder 200"), a tray 300, and a stand 400. The crimping device 100 includes a plurality of blades (not visible; described in further detail below) that define a channel 115 configured to receive a medical device in an expanded state, and an actuating member 105 operably coupled to the blades. The actuating member 105 can be manipulated by a user to vary or reduce a cross-sectional dimension (e.g., a diameter) of the channel 115 and, thereby, reduce the outer dimension of the medical device positioned within the channel 115. In some embodiments, the holder 200 is releasably coupled to the medical device, and then detachably coupled to an entry side 101 of the crimping device 100 such that the holder 200 positions the medical device appropriately within the channel 115 of the crimping device 100 before and/or during crimping.

As shown in FIG. 1, the crimping device 100 can be positioned at least partially within a reservoir 310 in the tray 300. In some embodiments, the tray 300 includes a plurality of flanges 305 that project into the reservoir 310 and define a recess 315 that is sized and shaped to retain the crimping device 100 such that the channel 115 is positioned within the reservoir 310. In other embodiments, the tray 300 can include different or additional features for retaining and appropriately positioning the crimping device 100 within the tray 300, such as fasteners, interlocking surfaces, and/or other suitable retention features. The reservoir 310 can hold a liquid (e.g., chilled saline) that submerges the channel 115 when the crimping device 100 is positioned within the recess 315. As further shown in FIG. 1, the tray 300 can also include an aperture 320 for receiving a portion of a delivery system 600 therethrough and to facilitate loading the crimped medical device into the delivery system 600. For example, an elongated catheter body 605 and/or delivery capsule 610 of the delivery system 600 can be inserted through the aperture 320 and positioned adjacent to the channel 115 on an exit side 103 of the crimping device 100. In some embodiments, the tray 300 can further include one or more sealing members (not shown) positioned within the aperture 320 to at least partially seal liquid within the reservoir 310 when the delivery system is moved into and out of the reservoir 310. The stand 400 can be positioned to support a portion of the catheter body 605 and/or align the delivery system 600 with the aperture 320 of the tray 300. In other embodiments, the system 10 can include additional components or some of the features may be omitted.

In operation, the crimping device 100 is positioned within the recess 315 of the tray 300. A medical device, such as a prosthetic heart valve device, is releasably attached to the holder 200 while the medical device is in its expanded state (e.g., an unconstrained state), and then the holder 200 is attached to the entry side 101 of the crimping device 100 such that the medical device extends into the channel 115. In some embodiments, the holder 200 is attached to the entry side 101 of the crimping device 100 before the crimping device 100 is positioned within the recess 315 of the tray 300. In some embodiments, the medical device can be packaged with and pre-attached to the holder 200. In some embodiments, the holder 200 is omitted, and the medical device can be placed in the channel 115 by itself and/or releasably attached to another portion of the crimping device 100 to retain the medical device in the channel 115. Before or after the medical device is positioned in the channel 115, the reservoir 310 of the tray 300 can be filled with a liquid (e.g., chilled saline) such that the channel 115 of the crimping device 100 and the medical device positioned therein are submerged in the liquid. Submerging the medical device can keep the medical device chilled as the crimping device 100 acts on the medical device to reduce the outer dimension of the medical device.

When the system 10 is used to facilitate loading of the device into the delivery system 600, a distal portion of the catheter body 605 can be positioned through the aperture 320 such that the delivery capsule 610 at the distal end of the catheter body 605 is positioned at the exit side 103 of the crimping device 100 adjacent the channel 115. In some embodiments, a distal nose cone of the delivery capsule 610 and an elongated central shaft attached thereto are inserted at least partly through the channel 115 and the unconstrained medical device (e.g., toward the entry side 101 of the crimping device 100 beyond a distal end of the medical device). The stand 400 can be positioned to support the catheter body 605 and/or other portions of the delivery system 600 outside of the tray 300, and to align the delivery system 600 with the aperture 320 of the tray 300 and the channel 115 of the crimping device 100.

Once the delivery system 600 and the medical device are properly positioned with respect to the crimping device 100, a user can manipulate the actuating member 105 of the crimping device 100 to reduce the cross-sectional dimension of the channel 115, and thereby reduce the outer dimension of the medical device (i.e., "crimp" the medical device). In some embodiments, the medical device is crimped to accommodate sizing of the delivery capsule 610 for implanting the medical device using a minimally invasive procedure. In some embodiments, reducing the cross-sectional dimension of the channel 115 disengages the holder 200 from the medical device such that the medical device is no longer attached to the holder 200 to allow for subsequent removal of the medical device from the channel 115 (e.g., via the exit side 103 or the entry side 101 of the crimping device 100).

Once the medical device has been crimped, the medical device can be loaded into the delivery system 600 for subsequent delivery to a patient. For example, a portion of the delivery system 600 can be configured to engage the medical device and pull the crimped medical device into the delivery capsule 610 and/or the catheter body 605. In some embodiments, a piston device of the delivery system 600 engages with features of the medical device, and is then retracted to pull the medical device into the delivery capsule 610. In some embodiments, the channel 115 of the crimping device 100 has a generally funnel-like shape in which the diameter of the channel 115 decreases along an axis from the entry side 101 to the exit side 103 (i.e., away from the holder 200 and toward the delivery capsule 610. In such embodiments, pulling the medical device into the delivery capsule 610 can further crimp a portion of the medical device as the medical device is pulled from a wider-diameter portion of the channel 115 and through a narrower-diameter portion of the channel 115. In some embodiments, the medical device is pulled into the delivery system 600 while submerged in the liquid within the reservoir 310. This is expected to inhibit air pockets or air bubbles from forming in the delivery system 600 as the medical device is loaded. Once the medical device is loaded in the delivery system 600, the delivery system 600 can be withdrawn from the tray 300 and subsequently used to implant the medical device in a patient. In some embodiments, the system 10 is configured to be a completely disposable system. Accordingly, the various components of the system 10, including the crimping device 100, can be disposed of (as compared to being cleaned for subsequent re-use) after the medical device is loaded into the delivery system. By making the system 10 disposable, the system 10 can be provided as a new, sterile environment prior to each procedure.

Selected Embodiments of Crimping Devices, Medical Device Holders, and Associated Methods FIGS. 2 and 3 are isometric views of the crimping device 100 of FIG. 1 illustrating the crimping device 100 in a first position with the channel 115 having a first cross-sectional dimension (FIG. 2) and in a second position with the channel 115 having a second cross-sectional dimension (FIG. 3). FIG. 4 is an isometric partially exploded view of the crimping device 100 of FIG. 2 (i.e., showing the crimping device 100 in the first position). In some embodiments, the first and second cross-sectional dimensions are a maximum and a minimum cross-sectional dimension, respectively. The crimping device 100 includes a frame 110, a plurality of movable blades 140 arranged circumferentially within the frame 110 to define the channel 115 having a central axis 107 extending therethrough.

Referring to FIG. 4, the frame 110 can include a first plate 120 having a plurality of first slots 122 extending through portions of the first plate 120, and a second plate 130 having a plurality of second slots 132 extending through portions of the second plate 130 (collectively referred to as "plates 120, 130"). The crimping device 100 further includes a first movable member 160 and a second movable member 170 (collectively "movable members 160, 170") that are movable (e.g., rotatable) with respect to the first and second plates 120 and 130. For example, the movable members 160, 170 can be configured to rotate about the central axis 107 of the channel 115. The first movable member 160 is positioned between the blades 140 and the first plate 120, and the first movable member 160 includes a plurality of third slots 162 extending through portions of the first movable member 160. Similarly, the second movable member 170 is positioned between the blades 140 and the second plate 130, and the second movable member 170 includes a plurality of fourth slots 172 extending through portions of the second movable member 170. Portions of the first slots 122 can be aligned with portions of the third slots 162, and portions of the second slots 132 can be aligned with portions of the fourth slots 172. In some embodiments, the first and second slots 122 and 132 (collectively referred to as "slots 122, 132") and the third and fourth slots 162 and 172 (collectively referred to as "slots 162, 172") are reflectively symmetric about a plane extending perpendicularly to the central axis 107 of the channel 115.

Each blade 140 can include a pin 142 that projects from a portion of the blade 140 spaced apart from the central axis 107 (e.g., an outer portion of the blade 140). At the exit side 103 of the crimping device 100, each pin 142 extends through one of the first slots 122 of the first plate 120 and a corresponding one of the third slots 162 of the first movable member 160, and at the entry side 101 of the crimping device 100 each pin 142 extends through one of the second slots 132 and a corresponding one of the fourth slots 172 of the second movable member 170. Accordingly, the quantity of slots 122, 132, 162, 172 on each of the plates 120, 130 and the movable members 160, 170 can correspond to the quantity of blades 140. In operation, a user can manipulate the actuating member 105 to rotate, slide, or otherwise move the first and second movable members 160 and 170 relative to the first and second plates 120 and 130. This drives the pins 142 along paths defined by corresponding slots 122, 132, 162, 172, thereby driving the blades 140 radially inward to decrease the cross-sectional dimension of the channel 115 (FIG. 3). The radially inward movement of the blades 140 acts on an outer surface of a medical device (e.g., a prosthetic heart valve device) positioned within the channel 115 and, thereby, reduces the outer cross-sectional dimension (e.g., diameter) of the medical device to fit within a delivery capsule (e.g., the delivery capsule 610 of FIG. 1). In some embodiments, the second plate 130 and the second movable member 170 are omitted such that the relative movement of the first plate 120 and the first movable member 160 alone drive the inward motion of the blades 140.

The plates 120, 130 can have a generally rectangular shape such that the frame 110 has a generally rectangular cross-section. In other embodiments, the plates 120, 130 can have other shapes such as, for example, circular, hexagonal, polygonal, etc., and can have different shapes from one another. For example, when the plates 120, 130 have a circular shape, the frame 110 can include a stabilizing base region. In some embodiments, the plates 120, 130 can be internal components positioned within an outer housing that defines the frame 110. The frame 110 can have a shape configured to fit snugly within the recess 315 (FIG. 1) of the tray 300. The actuating member 105 can be positioned on an upper surface 112 (FIG. 2) of the frame 110 such that it is accessibly to a user during a crimping procedure. In other embodiments, the actuating member 105 may be positioned elsewhere on the frame 110, or may be an electric motor instead of a manual actuator. As shown in FIG. 4, the plates 120, 130 are stationary relative to the movable members 160, 170. In some embodiments, the first plate 120 is movable relative to the first movable member 160 and/or the second plate 130 is movable relative to the second movable member 170 to drive the blades 140 radially inward. For example, manipulating the actuating member 105 can rotate the first plate 120 in an opposite direction as the first movable member 160.

The first and second slots 122 and 132 can each define a straight path extending radially away from the central axis of the channel 115. As shown in FIG. 4, each plate 120, 130 can include twelve slots 122, 132 spaced at equal intervals around the central axis 107 of the channel 115. However, in some embodiments, each plate 120, 130 can include fewer than or more than twelve slots (e.g., six slots, eight slots, fourteen slots, etc.) depending on the quantity of blades 140, and/or the slots 122, 132 can be arranged in other configurations and can have different shapes. For example, one or more of the slots 122, 132 can define a generally arcuate or other path. As illustrated in FIG. 4, the second slots 132 can have generally similar features to the first slots 122. In other embodiments, the second slots 132 can have a different number and/or have a different configuration, shape, etc. from the first slots 122.

The third slots 162 on the first movable member 160 can each define an arcuate or angled path having a first end 163a and a second end 163b spaced radially closer to the central axis of the channel 115 than the first end 163a. In some embodiments, the first movable member 160 includes twelve arcuate slots 162 spaced apart from each other at equal intervals around the central axis 107 of the channel 115. In other embodiments, the plurality of third slots 162 can include fewer than or more than twelve slots (e.g., eight slots) depending on the quantity of blades 140, and can be arranged in other configurations and can have different shapes. For example, the third slots 162 can define a generally straight path, or could have a concave portion that faces radially outward from the central axis of the channel 115. Although partly obscured in FIG. 4, the fourth slots 172 can have generally similar features to the third slots 162. In some embodiments, the slots 162, 172 are reflectively symmetric about a plane extending perpendicularly to the central axis 107 of the channel 115. In other embodiments, the slots 162, 172 can each comprise a different number of slots, and/or have different configurations, shapes, etc. from one another. Moreover, as shown in FIG. 4, the slots 162, 172 can be longer than the slots 122, 132 in the plates 120, 130. In some embodiments, the slots 162, 172 extend radially the same or a substantially similar distance as the slots 122, 132.

The first through fourth slots 122 132, 162, 172 define a path of movement for the pins 142. For example, the first and second slots 122 and 132 can be sized and shaped to maintain the position of the individual blades 140 relative to each other, and the third and fourth slots 162 and 172 can be sized and shaped to drive the blades 140 radially inward or outward. Accordingly, movement of the pins 142 along the slot paths causes the blades 140 to slide relative to each other and to move radially inward or outward. For example, movement of the first movable member 160 relative to the first plate 120 drives the pins 142 along the path defined by the third slots 162 of the first movable member 160 and constrained by the path of the first slots 122 of the first plate 120. Similarly, movement of the second movable member 170 relative to the second plate 130 drives the pins 142 along the path defined by the fourth slots 172 of the second movable member 170 and constrained by the path of the second slots 132 of the second plate 130. When the pins 142 are in an initial or first pin position (FIG. 2), the blades 140 are arranged such that the channel 115 has a maximum cross-sectional dimension (e.g., diameter), and the pins 142 are positioned at a radially outer end 123a (FIG. 2) of the first slots 122 and a radially outer end 162a (FIG. 4) of the third slots 162. When the pins 142 are in a final or second pin position (FIG. 3), the pins 142 are positioned at a radially inner end 123b (FIG. 3) of the first slots 122 and a radially inner end 162b (FIG. 4) of the third slots 162, and the channel 115 has a minimum cross-sectional dimension. Accordingly, the pins 142 can move between the first and second pin positions to reduce and expand the cross-sectional dimension of the channel 115. In other embodiments, the pins 142 can be positioned at different locations (e.g., positioned at an intermediate location) along the first slots 122 when in the first and/or second pin configuration. When the medical device is positioned within the channel 115, driving the pins 142 radially inward can reduce a cross-sectional dimension (e.g., diameter) of the medical device. In some embodiments, such as embodiments including twelve blades 140, the blades 140 are configured to reduce an outer diameter of a prosthetic heart valve device from about 1.67 inches (42.42 mm) to 0.4 inch (10.16 mm) or less. For example, the blades 140 can be configured to completely close the channel 115 in the second pin position (i.e., a cross-sectional dimension of the channel 115 is zero). As another example, in embodiments including eight blades 140, the blades 140 can be arranged such that the channel 115 has a maximum outer diameter of about 1.3 inches (33.02 mm) and can reduce the diameter of the channel 115 to 0.4 inch (10.16 mm) or less. The maximum and minimum cross-sectional dimensions of the channel 115 can depend on the quantity of blades 140, the size and shape of the blades 140, the locations of the pins 142 on the blades 140, and/or the travel path of the blades 140 as defined by the slots 122, 132, 162, 172.

As shown in FIG. 4, the second plate 130 includes a plurality of first connective features 133 and a plurality of second connective features 135. The first connective features 133 can be holes, flanged surfaces, and/or other attachment mechanisms configured to releasably couple the medical device holder 200 (FIG. 1) to the second plate 120 of the frame 110. The second connective features 135 are configured to provide an attachment mechanism for forming the frame 110 (e.g., connecting the first plate 120 to the second plate 130). As shown, the second connective features 135 can be hooks or fasteners shaped to mate with corresponding holes 125 on the first plate 120. In some embodiments, the second connective features 135 permit the frame 110 of the crimping device 100 to be taken apart to, for example, permit cleaning of the individual components within the frame (e.g., the blades 140 and movable members 160, 170). In some embodiments, the first and second plates 120 and 130 can be fixedly attached to each other via bonding, welding, and/or other attachment methods.

As further shown in FIG. 4, the crimping device 100 can also include an actuator device 150 operably coupled to the first and second movable members 160 and 170, and configured to move the first and second movable members 160, 170 relative to the first and second plates 120 and 130. In some embodiments, as shown in FIG. 4, the actuator device 150 includes the actuating member 105 coupled to a threaded shaft 152 and a connector 154 having a threaded shaft 156 extending therethrough. The connector 154 couples to portions of the first and second movable members 160, 170. Turning the actuating member 105 rotates the threaded shaft 152 about a longitudinal axis of the threaded shaft 152, which in turn moves the connector 154 along the length of the threaded shaft 152. Movement of the connector 154 moves the first and second movable members 160, 170, thereby driving the pins 142 inward or outward along the paths defined by the slots 122, 132, 162, 172 of the plates 120, 130 and the movable members 160, 170. For example, a user can turn the actuating member 105 in a first direction to cause the connector 104 to move downwards (i.e., towards the bottom of the page) in order to rotate the first and second movable members 160, 170 clockwise about the central axis 107 of the channel 115. Clockwise rotation of the first and second movable members 160, 170 can drive the pins 142 inward along the combined paths of the first and third slots 122, 162 and second and fourth slots 132, 172 to reduce the cross-sectional dimension of the channel 115. Turning the actuating member 105 in the opposite direction can rotate the movable members 160, 170 in the counterclockwise direction to drive the pins 142 outward along the combined paths of the first and third slots 122, 162 and second and fourth slots 132, 172 to increase the cross-sectional dimension of the channel 115. In some embodiments, the actuator device 150 can be configured to rotate the blades 140 in the opposite directions to effectuate device compression. The actuator device 150 illustrated in FIG. 4 provides for continuous (e.g., rather than stepwise) compression of a medical device placed within the channel 115 of the crimping device 100, and can have a relatively smaller footprint as compared to other types of actuators.

In some embodiments, the actuator device 150 can comprise a different mechanism to drive movement of the movable members 160, 170, and/or the actuator device 150 can be coupled to the movable members 160, 170 in a different manner. For example, in some embodiments, the actuator device 150 can comprise a lever coupled to the movable members 160, 170. In other embodiments, the movable members 160, 170 can be configured to slide (i.e., rather than rotate) relative to the plates 120, 130. In such embodiments, the actuator device 150 may comprise a handle or other gripping mechanism for sliding the movable members 160, 170. In still other embodiments, the actuator device 150 may include an electric motor configured to move the movable members 160, 170.

Figure 5:
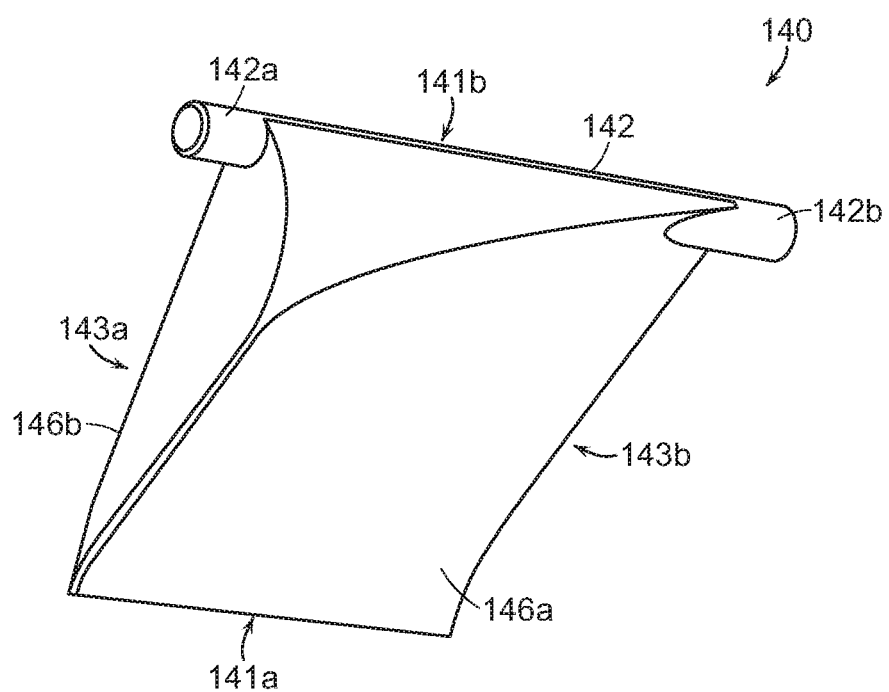
FIG. 5 is an isometric view of a blade of the crimping device shown in FIGS. 2-4 configured in accordance with some embodiments of the present technology.

FIG. 5 is an isometric view of one of the blades 140 of the crimping device 100 (FIGS. 1-4). Each blade 140 can include a first end portion 141a, a second end portion 141b, a first side 143a, and a second side 143b. The pin 142 of each blade 140 can include a first pin portion 142a projecting from the first side 143a of the blade 140 (e.g., toward the entry side 101 of the crimping device 100 of FIGS. 1-4), and a second pin portion 142b projecting from the second side 143b of the blade 140 (e.g., toward the exist side 103 of the crimping device 100 of FIGS. 1-4). The first pin portion 142a and the second pin portion 142b (collectively referred to as "pin portions 142a, 142b") can be a single component (e.g., a single shaft) extending through and/or integrally formed with the blade 140, or the pin portions 142a, 142b can be separate pin components that project from either side of the blade 140. In some embodiments, some or all of the blades 140 can include only the first pin portion 142a or only the second pin portion 142b. As shown in FIG. 5, the pin portions 142a, 142b project from the second end portion 141b of the blade 140. When the blade 140 is positioned within the crimping device 100, the second end portion 141b is spaced apart from and radially farther from the central axis 107 of the channel 115 than the first end portion 141a. Accordingly, the pin portions 142a, 142b project from a radially outer portion of the blade 140. Compared to a blade with a pin positioned at a central or more radially inward position of the blade, this radially outward positioning of the pin 142 requires less actuation (i.e., the pin 142 need not be driven as far) to produce an equal amount of inward movement of the blade 140. As a result, the overall size of the crimping device 100 is reduced while still maintaining a sufficiently large crimping range (e.g., the range between a minimum and maximum cross-sectional dimension of the channel 115) to accommodate the sizing of a medical device in an expanded state and the sizing of a delivery system (e.g., a delivery capsule).

As further shown in FIG. 5, the blade 140 includes an inner surface 146a and an outer surface 146b. In general, the inner and outer surfaces 146a and 146b are configured to enable adjacent blades 140 to slide relative to one another and to define a shape of the channel 115 of the crimping device 100. More specifically, the inner surface 146a can be generally sloped along an axis extending between the first and second sides 143a and 143b of the blade 140 (e.g., along the central axis 107 of the channel 115 shown in FIGS. 2-4).

The outer surface 146b can have a portion that is generally shaped to match the shape of the inner surface 146a of an adjacent blade 140, and is configured to slide against the inner surface 146a of an adjacent blade 140 as the pin portions 142a, 142b are actuated (e.g., driven radially inward or outward along the slots 122, 132 and slots 162, 172).

Figure 8:
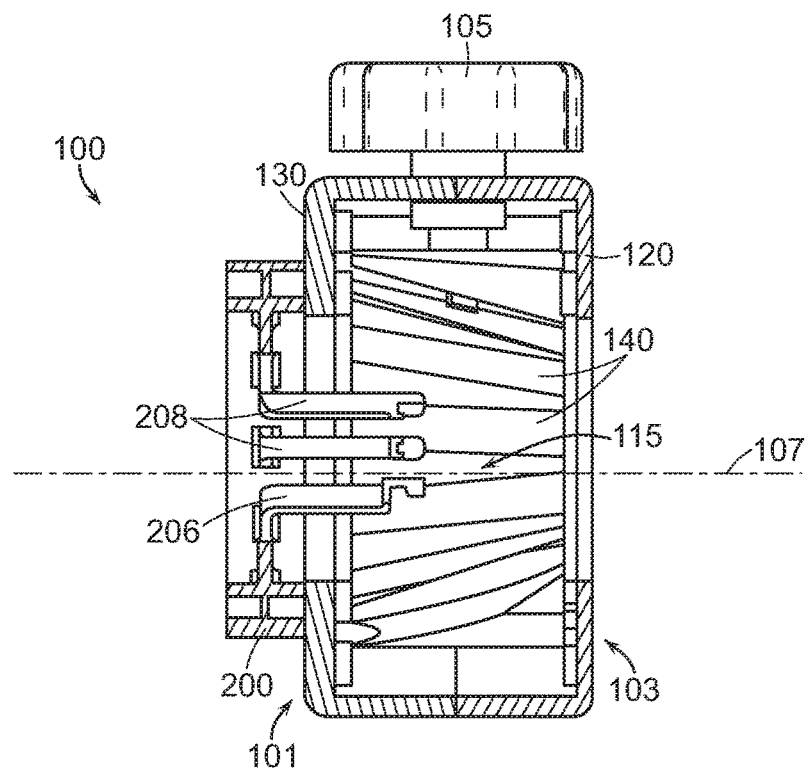

A portion of the inner surfaces 146a (e.g., a portion not covered by the outer surface 146b of an adjacent blade 140) of the blades 140 collectively define the channel 115 of the crimping device 100. When the blades 140 with a sloped inner surface 146a are arranged circumferentially, the channel 115 can have a generally funnel-like shape (e.g., as shown in FIG. 8). That is, the channel 115 can have a larger cross-sectional dimension closer to the second sides 143b of the blades 140 (e.g., proximate to the second plate 130 at the entry side 101 of the crimping device 100) than the first sides 143a of the blades 140 (e.g., proximate the first plate 120 at the exit side 103 of the crimping device). In other embodiments, the inner and outer surfaces 146a, 146b of the blade 140 can have other shapes or arrangements. For example, the inner surfaces 146a of each blade can have a wedge-like shape such that the channel 115 has a constant cross-sectional dimension along the central axis of the channel 115. In yet other embodiments, the blades 140 can generally have any other shape or configuration so as to form a channel 115 with a varying cross-sectional dimension along the central axis 107 of the channel 115. In some embodiments, the inner and/or outer surfaces 146a, 146b of the blade 140 can include one or more grooves, slots, holes, etc. These features can reduce the weight of the blade 140 to thereby increase the portability of the crimping device 100, without affecting the function or strength of the crimping device 100.

In some embodiments of the present technology, the crimping device 100 can omit one or more of the components described above with reference to FIGS. 2-5. For example, the crimping device 100 can include only one of the movable members 160, 170, and each blade 140 may include only one of the pin portions 142a or 142b to drive the blades 140 inward to reduce the size of a medical device. However, redundancy of the two movable members 160, 170 and the two plates 120, 130 at the first and second sides 101 and 103 of the crimping device 100 effectively supports each blade 140 at both the first and second side 143a, 143b of the blade 140. Including two movable members 160, 170 can also decrease the amount of force required to actuate the blades 140, and can facilitate at least substantially equal distribution of the actuating force across the blades 140 between the first and second sides 143a, 143b. In some embodiments, the crimping device 100 can include fewer than twelve blades (e.g., four blades, five blades, six blades, eight blades, etc.) or more than twelve blades (e.g., sixteen blades, twenty blades, etc.), and the quantity of slots 122, 132, 162, 172 of the movable members 160, 170 and the plates 120, 130 can be modified to correspond to the number of blades 140.

Each of the components described above with reference to FIGS. 2-5 can be made from the same or different materials, such as metals, polymers, plastic, composites, combinations thereof, and/or other materials. The components of the crimping device 100 can be manufactured using suitable processes, such as, for example, three-dimensional printing, injection molding, and/or other processes for supporting and compressing a medical device during a crimping procedure. In some embodiments, each component is made from a suitable plastic or polymer such that the system is completely disposable and able to be manufactured at a relatively low cost. In some embodiments, some of the components illustrated herein as individual components can be integrally formed together or otherwise combined.

In use, the crimping device 100 can provide a compact, yet efficient mechanism for reducing the size of a prosthetic heart valve device or other medical device. The slots 122, 132 of the plates 120, 130 and the slots 162, 172 of the movable members 160, 170 define paths for the pins 142 that slide the blades 140 radially inward relative to each other to reduce the diameter of the channel 115. This radially inward force is continuous along the surfaces of the blades 140 contacting the medical device within the channel 115, and therefore provides continuous compression of the medical device. As such, the continuous compression allows the user to pause or terminate the crimping procedure at any time (i.e., not just at the maximum and minimum diameters of the channel 115). Further, the funnel-like shape of the channel 115 provided by the blade shape allows portions of the medical device to be compressed more than other portions during inward movement of the blades. For example, a larger portion of the medical device may be positioned in the larger portion of the channel 115 (e.g., toward the entry side 101 of the crimping device 100) and not undergo as much compression as the portion of the medical device positioned in the smaller portion of the channel 115 (e.g., toward the exit side 103 of the crimping device 100). This can inhibit the compressive crimping forces from moving the medical device laterally toward the entry side 101 of the crimping device 100 and help retain the medical device within the channel 115 during crimping. In addition, the position of the pins 142 on the outer portions of the blades 140 reduces the length of the pin travel path necessary for inward movement of the blades 140 to achieve the desired crimping range. For example, the pins 142 can travel a distance of 0.26 inch (6.604 mm) to reduce the channel diameter from about 1.3 inches to 0.4 inch or less. Thus, the arrangement of the pins 142, the blades 140, the movable members 160, 170, and the plates 120, 130, in conjunction with the actuator device 150, allows the crimping device 100 to have a compact size that can easily be moved by a clinician to and from a sterile field, while still providing for a large crimping range suitable for reducing the size of prosthetic heart valves to allow for percutaneous delivery of the device.

Figure 6:
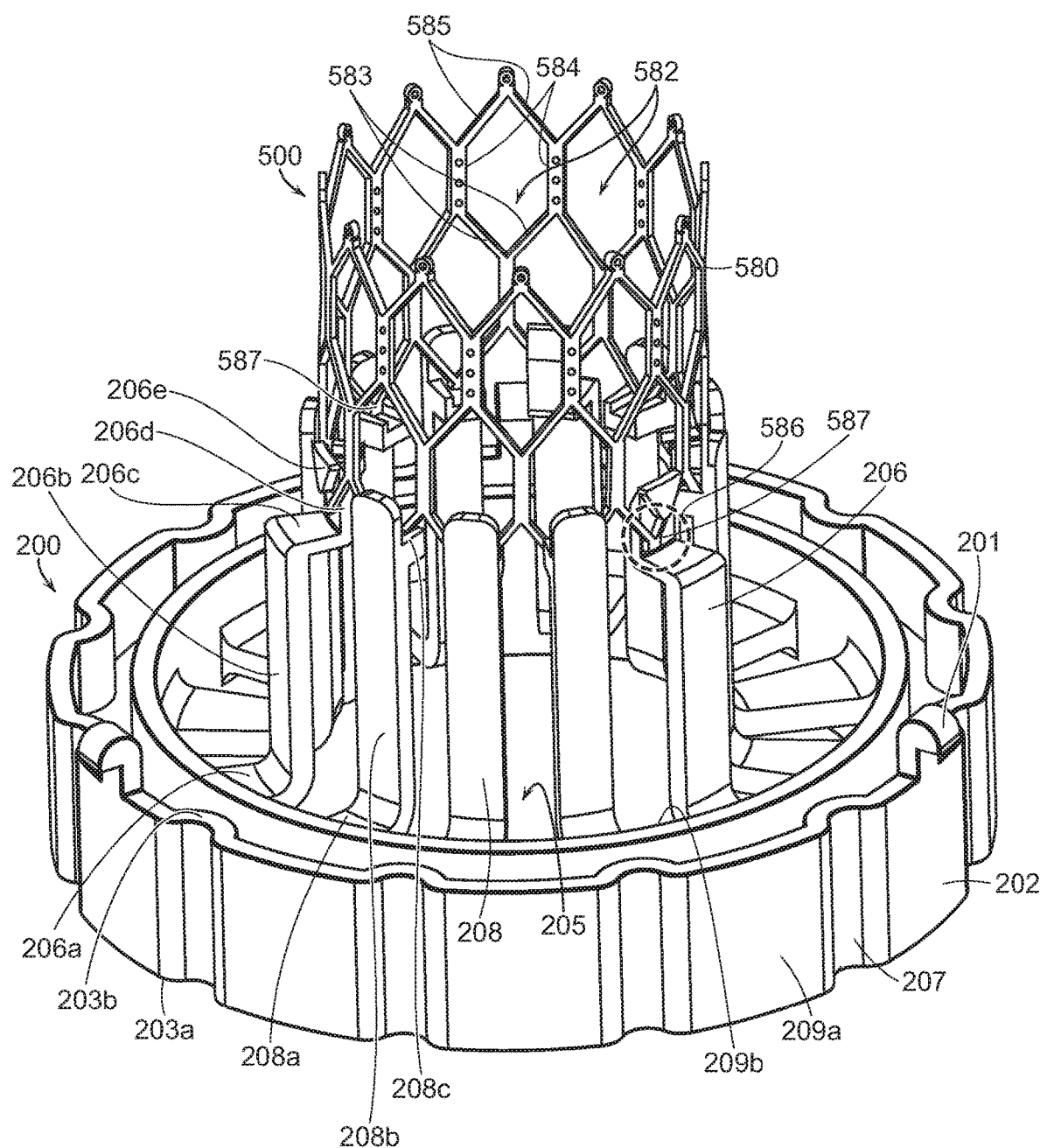
FIG. 6 is an isometric view of a medical device holder for use with the system shown in FIG. 1 and releasably coupled to a portion of a prosthetic heart valve device in accordance with some embodiments of the present technology.

FIG. 6 is an isometric view showing the medical device holder 200 ("holder 200") configured in accordance with an embodiment of the present technology and coupled to an exemplary medical device 500. In some embodiments as shown in FIG. 6, the medical device 500 is a valve support for use with a prosthetic heart valve device. The holder 200 includes a base 202 having a first side 203a, a second side 203b, and an opening 205 extending therebetween. The base 202 can include a plurality of connectors 201 on the second side 203b and configured to removably couple the holder 200 to the crimping device 100 (e.g., to the connective features 113 of the second plate 130 of FIGS. 2-4). As shown in FIG. 6, the base 202 can have a generally annular shape including a radially outer surface 209a and a radially inner surface 209b, both extending between the first and second sides 203a, 203b. The outer surface 209a can include a plurality of grooves 207 and/or ridges to make the holder 200 easy to grip and manipulate, even while submerged during the crimping process. The holder 200 further includes a plurality of first fingers 206 and a plurality of second fingers 208 (collectively "fingers 206, 208") projecting from the base 202 and arranged circumferentially around a central axis extending through the opening 205 of the base 202. The fingers 206, 208 are configured to engage at least a portion of the medical device 500 to hold the medical device 500 within the channel 115 of the crimping device 100 (FIGS. 2-4) during at least an initial portion of a crimping procedure.

As shown in FIG. 6, the first fingers 206 can be spaced around the central axis of the opening 205 to engage the medical device 500 at more than one point around a circumference of the medical device 500. The first fingers 206 include a first portion 206a extending radially inward from the inner surface 209b of the base 202 toward the central axis of the opening 205, a second portion 206b extending from the first portion 206a and away from the second side 203b of the base 202, a third portion 206c extending from the second portion 206b and radially inward toward the central axis of the opening 205, and a fourth portion 206d configured to engage the medical device 500. The fourth portion 206d can include an index feature 206e shaped to engage a portion of the medical device 500. For example, as shown in FIG. 6, the medical device 500 can be a stent-device including a frame 580 comprising a plurality of frame cells 582. Each frame cell 582 can have a hexagonal shape and comprise a pair of first struts 583, a pair of second struts 584, and a pair of third struts 585. Each of the first struts 583 can extend from an end of the second struts 584, and pairs of the first struts 583 can be connected together to form V-struts 586. At least some of the V-struts 586 at an end portion of the frame 580 can define an apex 587. As shown, the index features 206e can have a generally V-like shape to engage (e.g., mate with) an individual V-strut 586 of the medical device 500. In other embodiments, the medical device 500 and/or the first fingers 206 can have other suitable shapes that enable the first fingers 206 to engage a portion of the medical device 500. For example, the medical device 500 may be a stent device having frame cells 582 with a rectangular, sinusoidal, triangular, polygonal, or other shape, and the index features 206e can have a corresponding shape and arrangement that mates with or fits within a portion of the frame cells 582. In some embodiments, the first fingers 206 are configured to engage with the atrial end of a valve support of a prosthetic mitral valve device and/or other atrial portions of the prosthetic mitral valve device. In some embodiments, the first fingers 206 are configured to engage with the ventricular side of the valve support and/or other ventricular portions of the prosthetic mitral valve device.

In some embodiments, the first fingers 206 are flexible such that they bend radially inward or outward in response to external forces applied to the first fingers 206. For example, when the holder 200 is not attached to the medical device 500, the fourth portions 206d of the first fingers 206 can be positioned a distance away from the central axis of the opening 205 that is slightly greater than a cross-sectional dimension of the medical device 500. To attach the medical device 500, the first fingers 206 can be bent radially inward until the fourth portions 206d of the first fingers 206 are within the medical device 500, and then released. Accordingly, the index features 206e of the first fingers 206 can press against (e.g., the first fingers 206 are slightly radially biased outward against) a radially interior side of the medical device 500 to hold or grip the medical device 500. The index features 206e can prevent the medical device 500 from slipping off of the holder 200 when no other forces are applied to the first fingers 206. When the holder 200 is attached to the crimping device 100 (FIGS. 1-4), the blades 140 can press down on the first fingers 206 as the channel 115 decreases in size, thereby causing the first fingers 206 to flex inwardly and release the medical device 500 from the holder 200 for subsequent loading into the delivery system 600 (FIG. 1).

The second fingers 208 can each include a first portion 208a extending radially inward from the inner surface 209b of the base 202 toward the central axis of the opening 205, a second portion 208b extending from the first portion 208a and away from the second side 203b of the base 202, and a third portion 206c extending from the second portion 208b and radially inward toward the central axis of the opening 205. Notably, the first portion 208a of each second finger 208 is longer than the first portion 206a of each first finger 206. The second portions 206b of the first fingers 206 are therefore positioned radially farther from the central axis of the opening 205 than the second portions 208b of the second fingers 208. As shown, the third portions 208c of the second fingers 208 can be shaped and positioned to receive the apexes 587 of the medical device 500. The second fingers 208 can therefore provide additional support for holding the medical device 500 in place. In some embodiments, the holder 200 can include fingers 206, 208 with other shapes, arrangements, quantities, etc., suitable for holding the medical device 500 in place. For example, the holder 200 may comprise more or less than the twelve fingers 206, 208 shown in FIG. 6 (e.g., more or less than three first fingers 206 and more or less than nine second fingers 208). In some embodiments, the holder 200 includes only the first fingers 206 or only the second fingers 208.

Figure 7:
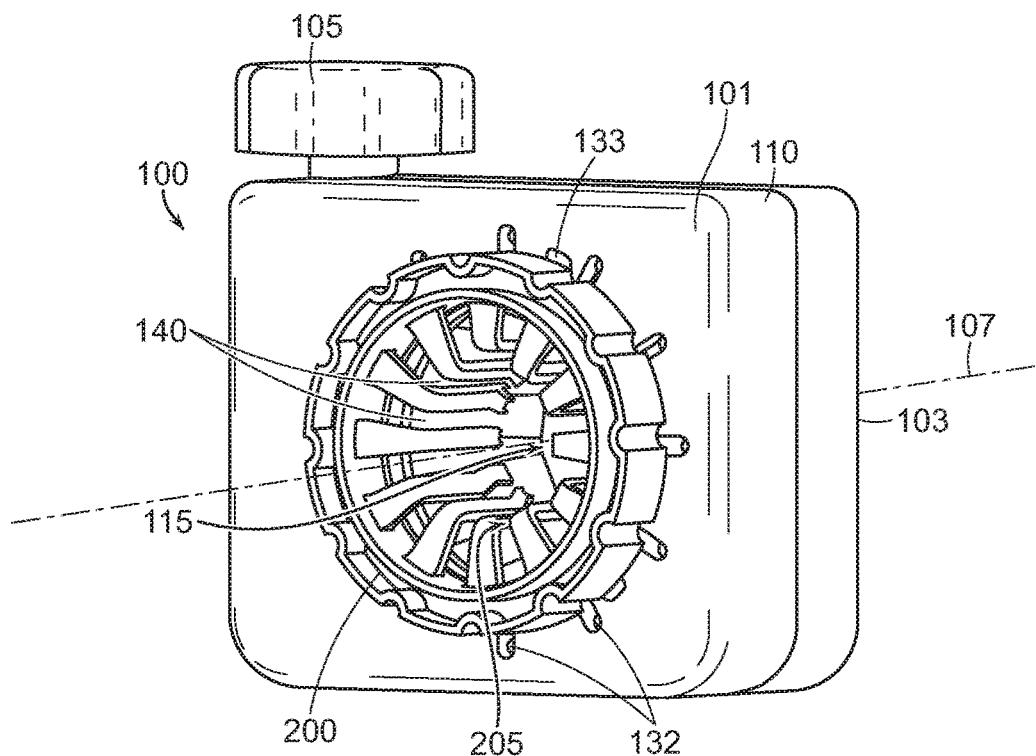
FIGS. 7 and 8 are an isometric view and cross-sectional view, respectively, illustrating the medical device holder of FIG. 6 coupled to the crimping device of FIGS. 2-4 in accordance with embodiments of the present technology.

FIGS. 7 and 8 are an isometric view and a cross-sectional side view, respectively, illustrating the holder 200 of FIG. 6 coupled to the crimping device 100 shown in FIGS. 2-4. For ease of illustration, the medical device 500 is not shown in FIGS. 7 and 8. Referring first to FIG. 7, the holder 200 can be removably coupled to the entry side 101 of the crimping device 100 via the second plate 130 of the frame 110. More specifically, the connectors 201 (shown in FIG. 6) of the holder 200 can connect to the first connective features 133 disposed on the frame 110. In some embodiments, the connectors 201 are at least one of hooks, fasteners, clips, locking features, etc. that engage (e.g., mate with) the first connective features 133 to removably secure the holder 200 to the crimping device 100. In some embodiments, the connectors 201 are inserted into the connective features 113, and the holder 200 is rotated to secure the holder 200 in place. Once secured, the central axis of the opening 205 of the holder 200 can be generally aligned with the central axis 107 of the channel 115 of the crimping device 100. By aligning the central axes of the crimping device 100 and holder 200, the medical device 500 can be evenly spaced with respect to the blades 140 within the channel 115 before the medical device 500 is crimped to facilitate generally symmetric radial compression of the medical device 500.

As shown in FIG. 8, the fingers 206, 208 of the holder 200 can project at least partly into the channel 115 of the crimping device 100. Accordingly, the fingers 206, 208 of the holder 200 can hold the medical device 500 (FIG. 6) in a position that is fully within the channel 115. FIG. 8 further shows an embodiment in which the channel 115 has a generally funnel-like shape in which a cross-sectional dimension (e.g., diameter) of the channel 115 decreases along the central axis 107 moving from the entry side 101 of the crimping device 100 to the exit side 103 of the crimping device 100.

Referring to FIGS. 6-8 together, to crimp the medical device 500, the actuating member 105 is manipulated as described above to reduce the diameter of the channel 115. As the diameter of the channel 115 decreases, portions of the blades 140 can contact portions of the first fingers 206 and/or portions of the second fingers 208 that are within the channel 115. Specifically, the blades 140 first contact the second portions 206b of the first fingers 206 because they are positioned radially farther from the central axis of the channel 115 than the second portions 208b (FIG. 6) of the second fingers 208. As the diameter of the channel 115 is further decreased, the blades 140 exert an inward force against the second fingers 208 that bends the fingers 208 radially inward and causes the fourth portions 206d of the first fingers 206 to disengage from the medical device 500. The blades 140 do not contact the first fingers 206 until after contacting the second fingers 208 because the second portions 208b of the second fingers 208 are positioned radially closer to the central axis 107 of the channel 115 than the second portions 206b of the first fingers 206. Therefore, after the first fingers 206 disengage from the medical device 500, the third portions 208c of the second fingers 208 can still engage and support a portion of the medical device 500 (e.g., the apexes 587). In some embodiments, the second fingers 208 can inhibit the medical device 500 from moving laterally (e.g., translation between the opposing plates 120, 130) while the medical device 500 is crimped. For example, the second fingers 208 can counteract the tendency of the medical device 500 to move laterally toward the entry side 101 of the crimping device 100 as a result of non-uniform compression of the medical device 500 caused by the funnel-like shape of the channel 115.

In some embodiments, the diameter of the channel 115 can be decreased to a small enough diameter to disengage the holder 200 from the medical device 500 (e.g., disengage the first fingers 206), but maintain a large diameter such that the fingers 206,208 positioned within the medical device 500 do not interfere with the crimping of the medical device 500. For example, the holder 200 and the crimping device 100 can be configured such that the holder 200: (i) holds (e.g., is engaged with and grips) the medical device 500 when the channel 115 of the crimping device 100 has a maximum diameter (e.g., the first position shown FIG. 2), and (ii) is disengaged from the medical device 500 when the channel 115 of the crimping device 100 has a minimum diameter (e.g., the second position shown FIG. 3). In some embodiments, the holder 200 can be removed from the crimping device 100 after the holder 200 disengages from the medical device 500. In such embodiments, the diameter of the channel 115 can then be further decreased to further crimp the medical device 500.

Selected Embodiments of Trays for Receiving a Crimping Device

Figure 9:
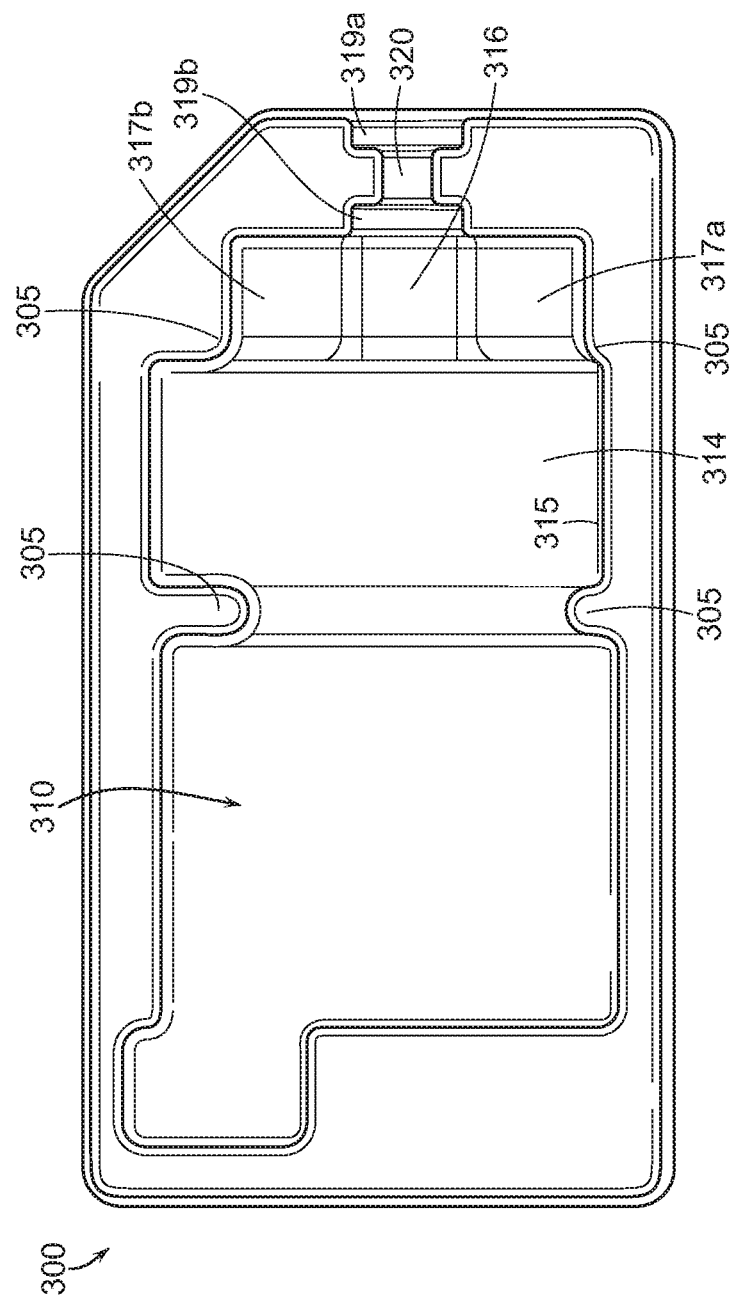
FIG. 9 is a top view of a tray of the system of FIG. 1 configured in accordance with various embodiments of the present technology.

FIG. 9 is a top view of the tray 300 of the crimping and loading system 10 of FIG. 1 configured in accordance with embodiments the present technology. The tray 300 can be formed using a thermoforming process and/or other suitable tray forming processes. As shown, the interior walls of the tray 300 define the reservoir 310 for holding a liquid (e.g., chilled saline). The reservoir 310 can include a first portion 312, a second portion 314, and a third portion 316. The first portion 312 can be sized and shaped to receive the crimping device 100 (FIGS. 1-4) with the entry side 101 or the exit side 103 facing down against a bottom surface of the tray 300 prior to use (e.g., during storage and/or shipping). The second portion 314 of the reservoir 310 is defined by the flanges 305 of the tray 300 and includes the recess 315 that is configured to retain the crimping device 100 (FIGS. 1-4) in a stable upright position during the crimping procedure. In some embodiments, the tray 300 includes a slot for introducing the liquid into the reservoir 310. The slot can be configured to allow liquid to enter the reservoir 310 in a non-turbulent manner, which is expected to inhibit air bubbles from forming in portions of the tray 300 or the crimping device 100. For example, in some embodiments, the slot provides a liquid flow path into the first portion 312 of the reservoir 310.

The third portion 316 of the reservoir 310 can be positioned at the exit side 103 of the crimping device 100 (e.g., as shown in FIG. 1), and can provide a region in which the crimped medical device can be loaded into a delivery system (e.g., the delivery system of FIG. 1). In some embodiments, the third portion 316 of the reservoir 310 can also provide an area to visualize the channel 115 of the crimping device 100 and/or portions of the delivery system positioned adjacent the crimping device 100 (FIG. 1) during device loading. For example, the tray 300 can include slanted sidewalls (identified individually as a first slanted sidewall 317a and a second slanted sidewall 317b; referred to collectively as "slanted sidewalls 317") on which one or more mirrors can be placed to provide alternate views of the crimping device 100 (FIGS. 1-4) and/or the delivery system. In some embodiments, the tray 300 has a generally flat lower surface in the third portion 316 with a mirror disposed on the lower surface to provide for visualization during device loading. The third portion 316 of the reservoir 310 can also be shaped to receive the stand 400 (FIG. 1) so that that the stand 400 can be positioned in the third portion 316 prior to use (e.g., during storage and/or shipping). Accordingly, in some embodiments, each component of the system 10 (FIG. 1) can be securely positioned within dedicated portions of the tray 300 for shipping and storage. The system 10 (FIG. 1) can therefore be provided to a physician in a streamlined and sterile manner.

As further shown in FIG. 9, the walls of the tray 300 further includes the aperture 320 for receiving a portion of a delivery system (e.g., the delivery system 600 of FIG. 1) therethrough, and one or more grooves (identified individually as a first groove 319a and a second groove 319b; referred to collectively as "grooves 319") positioned on either side the aperture 320. The grooves 319 can be configured to receive a dam member (not pictured) for sealing the reservoir 310 and preventing liquid from escaping through the aperture 320. In some embodiments, a portion of a suitable delivery system can puncture the dam members positioned within the grooves 319 in order to position the portion of the delivery system adjacent the crimping device 100 (FIG. 1). In some embodiments, the tray 300 can include valve and/or sealing device that is positioned on a sidewall of the tray 300 (e.g., in the aperture 320 or other hole) and in fluid communication with the reservoir 310. The valve and/or sealing device can fluidically seal liquid in the reservoir 310 before, during, and/or after a delivery system (e.g., the delivery system 600 of FIG. 1) has been moved therethrough. For example, a valve (e.g., a cross-slit valve, a one-way check valve, etc.) can be housed within a grommet (e.g., a molded silicone grommet) that is positioned in the hole in the sidewall of the tray 300 to at least partially prevent liquid from leaking from the reservoir 310 when the delivery system is moved into and out of the valve member. In other embodiments, the tray 300 can include other configurations of valves and/or sealing devices to seal liquid within the reservoir 310, while still allowing access to the reservoir 310 from a sidewall of the tray 300 for device loading or adjustment.

EXAMPLES

Several aspects of the present technology are set forth in the following examples.

1. A crimping device comprising:
a stationary plate having a plurality of first slots;
a movable member having a plurality of second slots, wherein the individual second slots are aligned with a portion of the corresponding individual first slots;
a plurality of movable blades arranged circumferentially to form a channel having a central axis extending therethrough, wherein—
each blade has a first end portion and a second end portion, and wherein the second end portion is radially farther from the central axis than the first end portion,
each blade includes a pin projecting from the second end portion of the blade, and
each pin extends through one of the first slots and a corresponding one of the second slots; and
an actuator device operably coupled to the movable member and configured to move the movable member relative to the stationary plate, wherein movement of the movable member drives the plurality of pins along a path defined by the first and second slots such that the plurality of blades move radially inward to decrease a diameter of the channel, and wherein the radial inward movement of the blades is configured to reduce a diameter of a medical device positioned within the channel to accommodate sizing of a delivery capsule for implanting the medical device using a minimally invasive procedure.

2. The crimping device of example 1 wherein the blades include a first side and a second side facing away from the first side, the stationary plate is a first stationary plate facing the first side of the blades, the movable member is a first movable member facing the first side of the blades, and each pin is a first pin on the first side of each blade, and wherein the crimping device further comprises:
a second stationary plate facing the second side of the blades, the second stationary plate having a plurality of third slots;
a second movable member facing the second side of the blades, the second movable member having a plurality of fourth slots,
wherein—
each blade includes a second pin projecting from the second end portion on the second side of the blade,
each second pin extends through one of the third slots and a corresponding one of the fourth slots, and
the actuator device is operably coupled to the first and second movable members and configured to move the first and second movable members relative to the first and second stationary plates to thereby actuate the plurality of blades to vary the diameter of the channel.

3. The crimping device of example 1 or 2 wherein the second slots define an arcuate path with a first end and a second end spaced closer to the channel than the first end.

4. The crimping device of any one of examples 1-3 wherein the diameter of the channel varies along the central axis.

5. The crimping device of any one of examples 1-4 wherein the blades have inner surfaces that define the channel, and wherein the inner surfaces are shaped such that the channel has a generally funnel-like shape.

6. The crimping device of any one of examples 1-5 wherein the plurality of blades includes twelve blades.

7. The crimping device of any one of examples 1-6 wherein— the movable member has a first position in which the channel has a maximum diameter, the movable member has a second position in which the channel has a minimum diameter, and the pins are positioned radially farther from the central axis in the first position than in the second position.

8. The crimping device of any one of examples 1-7, further comprising:

a frame; and a holder removably coupled to the frame and configured to hold the medical device within the channel as the blades reduce the diameter of the medical device.

9. The crimping device of example 8 wherein— the movable member has a first position and a second position, the channel has a smaller diameter in the second position than in the first position, and the holder includes a plurality of fingers configured to engage a portion of the medical device in the first position and configured to disengage from the portion of the medical device in the second position.

10. The crimping device of any one of examples 1-9 wherein the first slots define a straight path that extends radially away from the central axis.

11. The crimping device of any one of examples 1-10 wherein the second slots have a length that is longer than a length of the first slots.

12. The crimping device of any one of examples 1-11 wherein the first slots and second slots are equally spaced angularly around the central axis.

13. The crimping device of any one of examples 1-12, further comprising a connector coupled to the movable member and having a threaded hole extending therethrough, wherein— the movable member is a rotatable member, the actuator device is a threaded shaft and extends through the threaded hole of the connector, and actuating the rotatable member includes rotating the threaded shaft about a longitudinal axis of the shaft such that the connector moves along the shaft.

14. The crimping device of any one of examples 1-13 wherein the channel is configured to receive a prosthetic heart valve device for implantation into a native mitral valve, and wherein the blades are configured to reduce an outer diameter of the prosthetic heart valve device from 1.300 inches to 0.4 inch or less.

15. A system for reducing a size of a stent device, the system comprising:

a crimping device including— a frame having a stationary plate having a plurality of first slots, a movable member having a plurality of second slots, wherein the movable member is movable with respect to the stationary plate, a plurality of movable blades arranged circumferentially to define a channel having a central axis extending therethrough, wherein— the channel is configured to receive a prosthetic heart valve device in an unexpanded state, the movable member is between the blades and the stationary plate, each blade has a first end portion and a second end portion spaced radially farther from the central axis than the first end portion, each blade includes a pin projecting from the second end portion and extending through one of the first slots and a corresponding one of the second slots, and an actuator device configured to move the movable member to drive the plurality of blades between a first position in which the channel has a first cross-sectional dimension to a second position in which the channel has a second cross-sectional dimension smaller than the first cross-sectional dimension, wherein moving the blades from the first position to the second position decreases an outer dimension of the stent device, and wherein the first slots are configured to maintain relative position between the blades as the blades move between the first and second positions; and a holder removably coupled to the frame and configured to hold the stent device within the channel when the blades are in the first position.

16. The system of example 15 wherein the blades are configured to continuously compress the prosthetic heart valve device as the blades move from the first position to the second position.

17. The system of example 15 or 16 wherein the channel has a funnel shape.

18. The system of any one of examples 15-17, further comprising a tray defining a reservoir that is configured to receive the crimping device therein.

19. The system of example 18 wherein the reservoir is configured to hold a chilled liquid therein, and wherein the liquid fills the channel when the crimping device is positioned within the reservoir.

20. The system of example 18 wherein the tray includes an aperture extending through the tray to the reservoir, wherein the channel of the crimping device is accessible via the aperture to permit the prosthetic heart valve device to be positioned within the channel.

21. The system of any one of examples 15-20 wherein— the holder includes a plurality of fingers configured to engage attachment features of the prosthetic heart valve device in the first position; and the blades are sized and shaped to press against the fingers as the blades move from the first position to the second position to disengage the attachment features from the holder.

22. The system of any one of examples 15-21 wherein, in the first position, the pins are positioned radially farther from the central axis of the channel than in the second position.

23. A method for reducing a size of a medical device for loading into a delivery capsule, comprising:

positioning the medical device within a channel of the crimping device, wherein— the channel is defined by a plurality of movable blades arranged circumferentially around a central axis of the channel, each blade includes a pin projecting from an end portion of the blade spaced radially apart from the channel, and each pin projects through a first slot on a stationary plate and a second slot on a movable member positioned between the stationary plate and the blades; and driving the blades radially inwardly from a first position to a second position to reduce a cross-sectional dimension of the channel, thereby reducing an outer diameter of the medical device, wherein driving the blades includes moving the movable member relative to the stationary plate to move the pins along individual arcuate paths defined by the corresponding second slots.

24. The method of example 23 wherein driving the blades radially inwardly comprises driving the blades from the first position in which the channel has a minimum cross-sectional dimension of at least 1.300 inches to the second position in which the channel has a minimum cross-sectional dimension of at most 0.4 inch.

25. The method of example 23 or 24 wherein driving the blades radially inwardly comprises moving each pin from a first end of the arcuate path toward a second end of the arcuate path, wherein the second end is closer to the central axis of the channel than the first end.

26. The method of any one of examples 23-25 wherein driving the blades radially inwardly comprises continuously compressing the medical device.

27. The method of any one of examples 23-26 wherein the medical device is a prosthetic heart valve device, and wherein the method further comprises:
removably coupling a plurality of engagement features of the prosthetic heart valve device to a corresponding plurality of fingers of a holder, wherein the holder retains the prosthetic heart valve device while the blades are in the first position; and
wherein driving the blades radially inwardly presses the blades against outer surfaces of the fingers to disengage the engagement features from the holder.

28. The method of any one of examples 23-27 wherein the blades have inner surfaces that define the channel, wherein the inner surfaces are shaped such that the channel has a generally funnel-like shape, and further comprising:
after driving the blades to the second position, moving the medical device through the channel toward the delivery capsule to further reduce an outer diameter of the medical device.

29. The method of any one of examples 23-28, further comprising submerging the crimping device in a liquid such that the medical device is submerged when positioned within the channel.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A crimping device comprising:
a plate defining a plurality of first slots;
a movable member defining a plurality of second slots, wherein individual first slots are aligned with a portion of a corresponding individual second slot;
a plurality of blades arranged to form a channel having a central axis extending therethrough, wherein the movable member is disposed between the plate and the plurality of blades, wherein:
each blade includes a pin projecting from a radially outer end portion of the blade, and
each pin extends through one of the individual first slots and the corresponding individual second slot; and
an actuator configured to move the movable member relative to the plate to drive the plurality of pins along a path defined by the first and second slots such that the plurality of blades move radially inward to decrease a diameter of the channel.

2. The crimping device of claim 1, wherein the radially inward movement of the plurality of blades is configured to reduce a diameter of a medical device positioned within the channel.

3. The crimping device of claim 1, wherein each blade of the plurality of blades includes a first side and a second side facing away from the first side, the plate is a first plate facing the first sides of the blades, the movable member is a first movable member facing the first sides of the blades, and each pin is a first pin on the first side of each blade, and wherein the crimping device further comprises:
a second plate facing the second side of the blades, the second plate having a plurality of third slots;
a second movable member facing the second side of the blades, the second movable member having a plurality of fourth slots,
wherein:
each blade includes a second pin projecting from the radially outer end portion on the second side of the blade,
each second pin extends through one of the third slots and a corresponding one of the fourth slots, and
the actuator is further configured to move the second movable member relative to the second plate to actuate the plurality of blades to vary the diameter of the channel.

4. The crimping device of claim 1, wherein the second slots define an arcuate path with a first end and a second end spaced closer to the channel than the first end.

5. The crimping device of claim 1, wherein the diameter of the channel varies along a length the central axis.

6. The crimping device of claim 1, wherein the plurality of blades have inner surfaces that define the channel, and wherein the inner surfaces are shaped such that the channel has a generally funnel shape.

7. The crimping device of claim 1, wherein:
the movable member has a first position in which the channel has a maximum diameter and a second position in which the channel has a smaller diameter, and
the pins are positioned radially farther from the central axis in the first position than in the second position.

8. The crimping device of claim 1, wherein the first slots define a straight path that extends radially away from the central axis.

9. The crimping device of claim 1, wherein the second slots have a length that is longer than a length of the first slots.

10. The crimping device of claim 1, wherein the first slots and second slots are substantially equally spaced angularly around the central axis.

11. The crimping device of claim 1, further comprising a connector coupled to the movable member and having a threaded hole extending therethrough, wherein:
the movable member is a rotatable member,
the actuator device is a threaded shaft and extends through the threaded hole of the connector, and
wherein, to actuate the rotatable member, the actuator is configured to rotate the threaded shaft about a longitudinal axis of the shaft such that the connector moves along the shaft.

12. A system comprising:
a crimping device comprising:
a plurality of blades arranged to define a channel having a central axis extending therethrough, and
an actuator configured to cause the plurality of blades to move radially inward to decrease a diameter of the channel;
a holder configured to hold a medical device, the holder being removably coupled to the crimping device and being configured to insert the medical device into the channel; and
a tray defining a reservoir that is configured to receive the crimping device therein.

13. The system of claim 12, wherein, when the plurality of blades are movable by the actuator from a first position in which the channel has a first cross-sectional dimension to a second position in which the channel has a second cross-sectional dimension smaller than the first cross-sectional dimension.

14. The system of claim 13, wherein the plurality of blades are configured to continuously compress a prosthetic heart valve device disposed in the channel as the blades move from the first position to the second position.

15. The system of claim 12, wherein the reservoir is configured to hold a chilled liquid, and wherein the liquid fills the channel when the crimping device is positioned within the reservoir.

16. The system of claim 12, wherein the tray includes an aperture extending through the tray to the reservoir, wherein the channel of the crimping device is accessible via the aperture to permit a prosthetic heart valve device to be positioned within the channel.

17. A method for reducing a size of a medical device for loading into a delivery capsule, the method comprising:
positioning the medical device within a channel of a crimping device, wherein:
the channel is defined by a plurality of blades arranged around a central axis of the channel,
each blade includes a pin projecting from a radially outer end portion of the blade, and
each pin projects through a corresponding first slot in a plate and a corresponding second slot in a movable member positioned between the plate and the blades, wherein the plate comprises a plurality of first slots and the movable member comprises a plurality of second slots; and
moving the movable member relative to the plate to move the pins and drive the blades radially inwardly from a first position to a second position to reduce a cross-sectional dimension of the channel, thereby reducing an outer diameter of the medical device.

18. The method of claim 17, further comprising submerging the crimping device in a liquid such that the medical device is submerged when positioned within the channel.

19. The system of claim 12, wherein the crimping device comprises:
a frame comprising a plate defining a plurality of first slots; and
a movable member defining a plurality of second slots, wherein the movable member is movable with respect to the plate,
wherein each blade of the plurality of blades comprises a pin projecting from a radially outer end portion and extending through one of the first slots and a corresponding one of the second slots, and
wherein the actuator is configured to move the movable member to drive the plurality of pins along a path defined by the first and second slots such that the plurality of blades move radially inward from a first position to a second position to decrease the diameter of the channel, wherein the first slots are configured to maintain relative position between the blades as the blades move between the first and second positions.

* * * * *